US010590446B2

(12) United States Patent
Park et al.

(10) Patent No.: US 10,590,446 B2
(45) Date of Patent: Mar. 17, 2020

(54) MICROORGANISM FOR SIMULTANEOUSLY PRODUCING L-AMINO ACID AND RIBOFLAVIN, AND METHOD FOR PRODUCING L-AMINO ACID AND RIBOFLAVIN USING SAME

(71) Applicant: CJ CHEILJEDANG CORPORATION, Seoul (KR)

(72) Inventors: Sang Hee Park, Seoul (KR); Jun Ok Moon, Seoul (KR); Sang Jo Lim, Incheon (KR); Do Hyun Kwon, Ulsan (KR); Kyung Han Lee, Seoul (KR); Jin Suck Sung, Gyeonggi-do (KR); Hyun Joon Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 486 days.

(21) Appl. No.: 14/362,036

(22) PCT Filed: Oct. 17, 2012

(86) PCT No.: PCT/KR2012/008456
§ 371 (c)(1),
(2) Date: May 30, 2014

(87) PCT Pub. No.: WO2013/081296
PCT Pub. Date: Jun. 6, 2013

(65) Prior Publication Data
US 2014/0356518 A1 Dec. 4, 2014

(30) Foreign Application Priority Data

Dec. 1, 2011 (KR) .................. 10-2011-0127955

(51) Int. Cl.
C12P 13/08 (2006.01)
C12P 17/10 (2006.01)
C12P 25/00 (2006.01)
C12P 17/12 (2006.01)
C12R 1/15 (2006.01)
A23K 20/142 (2016.01)
C12N 1/20 (2006.01)

(52) U.S. Cl.
CPC ............ C12P 17/12 (2013.01); A23K 20/142 (2016.05); C12N 1/20 (2013.01); C12P 13/08 (2013.01); C12P 25/00 (2013.01); C12R 1/15 (2013.01); A23V 2002/00 (2013.01)

(58) Field of Classification Search
CPC ................................ C12P 13/08; C12P 25/00
USPC .................................................. 435/66, 115
See application file for complete search history.

(56) References Cited

U.S. PATENT DOCUMENTS 3,700,557 A * 10/1972 Nakayama et al. .... C12P 13/08
435/115
5,589,355 A * 12/1996 Koizumi ................. C12P 25/00
435/252.3
7,871,801 B2 1/2011 Ueda et al.
2007/0275438 A1 11/2007 David
2009/0004705 A1 1/2009 Kroger et al.
2009/0098598 A1 4/2009 Filho et al.
2009/0226571 A1 9/2009 Freyer et al.
2010/0317067 A1* 12/2010 Kim ..................... C12N 9/0008
435/115

FOREIGN PATENT DOCUMENTS

| CN | 1894411 A | 1/2007 | |
|---|---|---|---|
| EP | 0 969 096 A1 | 1/2000 | |
| EP | 1964923 A1 * | 9/2008 | ................ C12P 7/00 |
| EP | 2 192 170 A1 | 6/2010 | |
| JP | 6-225776 A | 8/1994 | |
| JP | 2007-043947 A | 2/2007 | |
| JP | 2007-513942 A | 5/2007 | |
| JP | 2007-167064 A | 7/2007 | |
| JP | 2009-506783 A | 2/2009 | |
| JP | 2011-510625 A | 4/2011 | |
| JP | 2011-182779 A | 9/2011 | |
| KR | 10-2004-0041576 A | 5/2004 | |
| KR | 10-2005-0018797 A | 2/2005 | |
| KR | 101335853 B1 | 12/2013 | |
| WO | WO 2003-029457 A1 | 4/2003 | |
| WO | 2005/059144 A1 | 6/2005 | |
| WO | 2010/052319 A1 | 5/2010 | |
| WO | WO 2011-004962 A2 | 1/2011 | |
| WO | WO 2013/081296 A1 | 6/2013 | |

OTHER PUBLICATIONS

Zhou et al., "Global analysis of gene transcription regulation in prokaryotes", Cell Mol Life Sci 63:2260-2290, 2006.*
Kozak, M. "Initiation of translation in prokaryotes and eukaryotes", Gene 234:187-208, 1999.*

(Continued)

Primary Examiner — David Steadman
(74) Attorney, Agent, or Firm — Cooley LLP

(57) ABSTRACT

The present invention relates to a method for producing highly-concentrated L-amino acid and riboflavin simultaneously, and a microorganism for simultaneously producing L-amino acid and riboflavin. Specifically, the present invention relates to a modified microorganism for producing L-lysine or L-threonine, and riboflavin simultaneously, wherein the microorganism belonging to *Corynebacterium* sp. capable of producing L-lysine or L-threonine is modified by enhancing the activity of an enzyme family expressed by a rib operon which contains riboflavin biosynthesis gene family. Also, the present invention relates to a method for the simultaneous production of L-lysine or L-threonine, and riboflavin using the modified microorganism, and relates to a formulation or granular formulation, feed, and feed additive, containing L-lysine or L-threonine, and riboflavin produced from a culture medium of the modified microorganism.

7 Claims, 4 Drawing Sheets
Specification includes a Sequence Listing.

(56) References Cited

OTHER PUBLICATIONS

Cai et al., "Improving the Clostridium acetobutylicum butanol fermentation by engineering the strain for co-production of riboflavin", J. Ind. Microbiol. Biotechnol. 38:1013-1025, Aug. 2011.*

Wang et al., "Enhancement of riboflavin production with Bacillus subtilis by expression and site-directed mutagenesis of zwf and gnd gene from Corynebacterium glutannicunn", Bioresource Tech. 102:3934-3940, 2011 (Year: 2011).*

Ikeda et al., "A novel methodology employing Corynebacterium glutamicum genome information to generate a new L-lysine-producing mutant", Appl. Microbiol. Biotechnol. 58:217-223, 2002 (Year: 2002).*

International Search Report issued by the Korean Intellectual Property Office for International Application No. PCT/KR2012/008456, dated Mar. 15, 2013, six pages.

Marx et al., "Metabolic phenotype of phosphoglucose isomerase mutants of Corynebacterium glutamicum," Journal of Biotechnology 104: 185-197, 2003.

Ohnishi et al., "A novel gnd mutation leading to increased L-lysine production in Corynebacterium glutamicum," FEMS Microbiology Letters 242: 265-274, 2005.

Perkins et al., "Genetic engineering of Bacillus subtilis for the commercial production of riboflavin," Journal of Industrial Microbiology & Biotechnology 22: 8-18, 1999.

Wittman and Heinzle, "Genealogy Profiling through Strain Improvement by Using Metabolic Network Analysis: Metabolic Flux Genealogy of Several Generations of Lysine-Producing Corynebacteria," Applied and Environmental Microbiology 68(12): 5843-5859, Dec. 2002.

European Patent Office, Extended European Search Report for European Patent Application No. EP 12852576.3, dated Jun. 5, 2015, nine pages.

Koizumi et al., "Production of riboflavin by metabolically engineered Corynebacterium ammoniagenes," Appl. Microbial. Biotechnol. 53: 674-679, 2000.

* cited by examiner

ND METHOD FOR

SEQUENCE LISTING

```
<160> NUMBER OF SEQ ID NOS: 17

<210> SEQ ID NO 1
<211> LENGTH: 4053
<212> TYPE: DNA
<213> ORGANISM: Corynebacterium glutamicum ATCC 13032
<220> FEATURE:
<221> NAME/KEY: gene
<222> LOCATION: (1)..(4053)
<223> OTHER INFORMATION: rib operon(NCgl1536~1532)

<400> SEQUENCE: 1
```

```
atggcacaac gtactccact aatcgcccca tccattcttg ctgctgattt ctcccgctta      60
ggggagcagg tgttggctgt tcctgatgct gactggattc acgtcgacat catgacggga     120
cacttcgttc caaacttgag ctttggcgcg gatatcacag ctgcggtcaa ccgcgttacg     180
gacaaagaac tagacgtcca cctgatgatc gaaaacccag agaagtgggt ggacaactac     240
atcgacgctg gcgcggactg cattgttttc cacgttgaag ccaccgaagg tcacgttgag     300
ttggctaagt acatccgttc caagggtgtg cgtgcaggtt tctccctgcg ccctggaact     360
cccatcgagg attacttgga tgacctcgag cacttcgatg aagtcatcgt catgagcgtc     420
gagcctggat tcggtggcca aagcttcatg cctgaacaac tggaaaaggt tcgtaccctg     480
cgcaaggtca tcgatgagcg cggtctgaac accgtcatcg agatcgacgg cggcattagc     540
gccaagacca tcaagcaggc tgccgacgct ggcgtggatg ccttcgttgc aggttccgct     600
gtgtacggcg ctgaggatcc caacaaggcg atccaggagt tgcgagcact cgcgcagtaa     660
atggatgttg cgcacgcgtt agatctggcc caccacgtgt cagatcaagt ccgaggcacc     720
accagcccta atccgccagt cggcgctgtc attttggacg ccgacggcga ggtcgttggc     780
gttggcgcca cggcacctcc tggtggcccg cacgccgaag tggtggcgct tgcagctgcc     840
ggagtgcgtg ccaacggggg cacggcggtg gtcaccctcg agccgtgcaa ccattacggc     900
cgcacgggtc catgttccaa ggcgcttctc gacgccggga tcgcacacgt gttttacgcc     960
aatgcggatc ccttcccgtc agccgctggg ggcggtgcct ttttggcgga ggcgggcgtc    1020
gatacgcatt ttttagatga gcggatcagg gcactggagc cctggctggt tgcgacgcgt    1080
ctgggcaggc cccatgtcac gttgaagttt gcgtccaccg tggacggttt tgctggtgcc    1140
accgatggca ccagccagtg gattaccggg ccggatgcgc gggcgtttgt gcacgaagat    1200
cgaagtaaaa gagatgcgat catcgtgggt accggtactg cgttgactga taatccctcc    1260
ttgacgcgc ggaccgatac gggtctttat gaaaatcaac ccaggcgcgt tgttattggc    1320
tcccgcgagg ttccagcaga ttccaacttg gctcgcttgg gatatgagca gtacgcggga    1380
ataccagagg ctttatcagc gctgtgggat aaagggtgcc gagacatttt aatcgaaggt    1440
ggcccaacgt tagctggggc agcgctgcgc ttaggcattg ttgatcaggt gcaggcctat    1500
gttgccccg ctttgttggg cgctggacga tcagtgatta actggccaca agaaaccacg    1560
atggatcaga ttatgcgttt tgacaccacg tccgtgagac agttgggttc agatgtattg    1620
atagaaatga tgagaaagga acactaaatg ttcacaggta ttgtcgagga gcttggctcc    1680
gttgcaggcg tggaacatct gggagattcc atccggatgc agatttccgc gtccaccgtt    1740
ttagagggtg tgcatttggg ggattccatt tctgtcaatg gtgtgtgctt gacagtggcg    1800
tcctttggcg agggacattt cactgcagac ctcatgcagg aaaccttaga tcgcagctcc    1860
ctgggcgcat tatccaccgg tagcaaagtc aaccttgagc gcgccatggc agccgatggc    1920
cgtctgggtg gacacatcat gcaaggccat gttgatgcca ccacctcgct gatcaagcgc    1980
accagctcag agaactggga tgttctgcgt tttgagctgc agctgatttt ggctcgctat    2040
gtggtggaaa aaggctccat cgcactcaat ggcacatcct tgactgtatc gtctttgggt    2100
gatgattggt ttgaggtttc cctgattccc accaccttgc gcgacaccac ccacggcgaa    2160
ctggcggtag gggatatcgt aaacattgag gttgatgtga tcgctaagta cgtcgaacgc    2220
atgatgacgc gcgcgtggc tggaaacact cccaatgact acaccgattt cacgagagac    2280
taggttagac aacgtgagtg aacatgagca ggcacacagc caattagatt ctgttgaaga    2340
```

```
ggccatcgct gacatcgctg cgggtaaagc cgtcgtggtg gtagatgatg aagatcgtga    2400
aaatgaaggc gacatcatct ttgccgccga attagccact ccagaattag tcgctttcat    2460
ggtgcgttat tcctcgggat acatctgtgc gccattaacc gcaaaggatg cagatcgtct    2520
tgatctgcct ccgatgaccg cgcacaatca ggatgcccgc ggcaccgctt acaccgtgac    2580
cgttgatgcc aacaccggca ccacaggcat ttctgcaaca gaccgcgccc acactttgcg    2640
cttgcttgct gatccagaag ccgaccgcac ggatttcacc cgtcccggac acgttgtgcc    2700
actgcgtgct cgtgaaggtg gcgtcttggt gcgcgctgga cacaccgaag cagctgtcga    2760
tttggctcgc gctgcaggcc tgcgcccagc aggtgttatc tgcgaagtgg tcagtgaaga    2820
ggaccccacc ggcatggctc gggttcctga gctgcgccgc ttctgcgatg agcacgatct    2880
gaagctgatc tctattgagc agctcattga gtggcgtcgc aagaatgaaa ttttggtgga    2940
gcgccaggtg gaaactgtgc tgcctaccga tttcggcacg ttcaaggctg ttggttaccg    3000
ttccatcatc gatggcaccg agcttgttgc cattgttgcc ggcgacgtgg catccgacgg    3060
tggcgaaaac gtcctggttc gagtccactc tgagtgcttg actggtgatg tttttggatc    3120
ccggcgctgc gactgtggac agcagctgca cgagtctttg cgcctgatcc aggaagctgg    3180
tcggggagta gtggtgtaca tgcgtgggca tgagggacga ggcattggtc tgctcgccaa    3240
gctacgcgcc taccaactcc aggatgaagg tgccgacacc gtcgatgcca acctcgcact    3300
tggtcttcca gccgatgccc gcgaatttgg caccagcgcc cagattctct acgacttggg    3360
tgtgcgctcg ctcaacttga tcagcaacaa cccagccaag aaggtgggac ttgaaggcca    3420
cggcatttcc attgccagcc gaaccccat ccctgttgct gttcatgaag acaatgttcg    3480
atacctgaaa accaagcgtg accgcatggg acatgacctc ccagatgtcg cactgtggga    3540
acaagagcac ccagaaaact aaggagcaca acaatggcta agaaggatt gccggcagtc    3600 gaactccccg acgccagcgg attaaaagtc gccgtagtca ccgcacggtg gaacgcagaa    3660
atctgcgacc gcctgcacaa gcacgcagta gatgcgggac gtgcagcagg agcaacggtg    3720
agcgaatacc gcgtcatcgg cgccctggaa cttccagtcg tagtgcaaga actggcacgc    3780
acccatgacg cagtagttgc cttgggctgt gtcgttcgtg gcggcacccc acactttgat    3840
tacgtgtgcg actctgtcac cgaaggcctc acccgcattg ctcttgatac ttccaccccca    3900 atcggcaacg gtgtgttgac taccaacacc gaagagcaag ccgtggaacg ctccggtgga    3960
gaaggctctg tagaggacaa aggcgcagag gcaatggtcg ctgcactcga tactgccctc    4020
gtgctttctc aaattcgtgc aactgagggt tag                                 4053
```

<210> SEQ ID NO 2
<211> LENGTH: 3393
<212> TYPE: DNA
<213> ORGANISM: Corynebacterium glutamicum ATCC 13032
<220> FEATURE:
<221> NAME/KEY: gene
<222> LOCATION: (1)..(3393)
<223> OTHER INFORMATION: riboflavin biosynthesis gene cluster
      (NCgl1535~1532)

<400> SEQUENCE: 2

```
atggatgttg cgcacgcgtt agatctggcc caccacgtgt cagatcaagt ccgaggcacc      60
accagcccta atccgccagt cggcgctgtc attttggacg ccgacggcga ggtcgttggc     120
gttggcgcca cggcacctcc tggtggcccg cacgccgaag tggtgcgct tgcagctgcc     180 ggagtgcgtg ccaacggggg cacggcgtg gtcaccctcg agccgtgcaa ccattacggc     240
```

-continued

```
cgcacgggtc catgttccaa ggcgcttctc gacgccggga tcgcacacgt gttttacgcc    300
aatgcggatc ccttcccgtc agccgctggg ggcggtgcct ttttggcgga ggcgggcgtc    360
gatacgcatt ttttagatga gcggatcagg gcactggagc cctggctggt tgcgacgcgt    420
ctgggcaggc cccatgtcac gttgaagttt gcgtccaccg tggacggttt tgctggtgcc    480
accgatggca ccagccagtg gattaccggg ccggatgcgc gggcgtttgt gcacgaagat    540
cgaagtaaaa gagatgcgat catcgtgggt accggtactg cgttgactga taatccctcc    600
ttgacggcgc ggaccgatac gggtctttat gaaaatcaac ccaggcgcgt tgttattggc    660
tcccgcgagg ttccagcaga ttccaacttg gctcgcttgg gatatgagca gtacgcggga    720
ataccagagg ctttatcagc gctgtgggat aaagggtgcc gagacatttt aatcgaaggt    780
ggcccaacgt tagctggggc agcgctcgc ttaggcattg ttgatcaggt gcaggcctat    840
gttgcccccg ctttgttggg cgctggacga tcagtgatta actggccaca agaaaccacg    900
atggatcaga ttatgcgttt tgacaccacg tccgtgagac agttgggttc agatgtattg    960
atagaaatga tgagaaagga acactaaatg ttcacaggta ttgtcgagga gcttggctcc   1020
gttgcaggcg tggaacatct gggagattcc atccggatgc agatttccgc gtccaccgtt   1080
ttagagggtg tgcatttggg ggattccatt tctgtcaatg gtgtgtgctt gacagtggcg   1140
tcctttggcg agggacattt cactgcagac ctcatgcagg aaaccttaga tcgcagctcc   1200
ctgggcgcat tatccaccgg tagcaaagtc aaccttgagc gccatggc agccgatggc    1260
cgtctgggtg gacacatcat gcaaggccat gttgatgcca ccacctcgct gatcaagcgc   1320
accagctcag agaactggga tgttctgcgt tttgagctgc cagctgattt ggctcgctat   1380
gtggtggaaa aaggctccat cgcactcaat ggcacatcct tgactgtatc gtctttgggt   1440
gatgattggt ttgaggtttc cctgattccc accaccttgc gcgacaccac ccacggcgaa   1500
ctggcggtag gggatatcgt aaacattgag gttgatgtga tcgctaagta cgtcgaacgc   1560
atgatgacgc gcggcgtggc tggaaacact cccaatgact acaccgattt cacgagagac   1620
taggttagac aacgtgagtg aacatgagca ggcacacagc caattagatt ctgttgaaga   1680
ggccatcgct gacatcgctg cgggtaaagc cgtcgtggtg gtagatgatg aagatcgtga   1740
aaatgaaggc gacatcatct ttgccgccga attagccact ccagaattag tcgctttcat   1800
ggtgcgttat tcctcgggat acatctgtgc gccattaacc gcaaaggatg cagatcgtct   1860
tgatctgcct ccgatgaccg cgcacaatca ggatgcccgc ggcaccgctt acaccgtgac   1920
cgttgatgcc aacaccggca ccacaggcat ttctgcaaca gaccgcgccc acactttgcg   1980
cttgcttgct gatccagaag ccgaccgcac ggatttcacc cgtcccggac acgttgtgcc   2040
actgcgtgct cgtgaaggtg gcgtcttggt gcgcgctgga cacaccgaag cagctgtcga   2100
tttggctcgc gctgcaggcc tgcgcccagc aggtgttatc tgcgaagtgg tcagtgaaga   2160
ggacccacc ggcatggctc gggttcctga gctgcgccgc ttctgcgatg agcacgatct   2220
gaagctgatc tctattgagc agctcattga gtggcgtcgc aagaatgaaa ttttggtgga   2280
gcgccaggtg gaaactgtgc tgcctaccga tttcggcacg ttcaaggctg ttggttaccg   2340
ttccatcatc gatggcaccg agcttgttgc cattgttgcc ggcgacgtgg catccgacgg   2400
tgcgaaaaac gtcctggttc gagtccactc tgagtgcttg actggtgatg tttttggatc   2460
ccggcgctgc gactgtggac agcagctgca cgagtctttg cgcctgatcc aggaagctgg   2520
tcggggagta gtggtgtaca tgcgtgggca tgagggacga ggcattggtc tgctcgccaa   2580
gctacgcgcc taccaactcc aggatgaagg tgccgacacc gtcgatgcca acctcgcact   2640
```

```
tggtcttcca gccgatgccc gcgaatttgg caccagcgcc cagattctct acgacttggg    2700
tgtgcgctcg ctcaacttga tcagcaacaa cccagccaag aaggtgggac ttgaaggcca    2760
cggcatttcc attgccagcc gaaccccat ccctgttgct gttcatgaag acaatgttcg     2820 ataccctgaaa accaagcgtg accgcatggg acatgacctc ccagatgtcg cactgtggga   2880
acaagagcac ccagaaaact aaggagcaca acaatggcta agaaggatt gccggcagtc    2940 gaactccccg acgccagcgg attaaaagtc gccgtagtca ccgcacgtgt gaacgcagaa    3000
atctgcgacc gcctgcacaa gcacgcagta gatgcgggac gtgcagcagg agcaacggtg   3060
agcgaatacc gcgtcatcgg cgccctggaa cttccagtcg tagtgcaaga actggcacgc   3120
acccatgacg cagtagttgc cttgggctgt gtcgttcgtg gcggcacccc acactttgat   3180
tacgtgtgcg actctgtcac cgaaggcctc acccgcattg ctcttgatac ttccacccca   3240
atcggcaacg gtgtgttgac taccaacacc gaagagcaag ccgtggaacg ctccggtgga   3300
gaaggctctg tagaggacaa aggcgcagag gcaatggtcg ctgcactcga tactgccctc   3360
gtgctttctc aaattcgtgc aactgagggt tag                                 3393

<210> SEQ ID NO 3
<211> LENGTH: 660
<212> TYPE: DNA
<213> ORGANISM: Corynebacterium glutamicum ATCC 13032
<220> FEATURE:
<221> NAME/KEY: gene
<222> LOCATION: (1)..(660)
<223> OTHER INFORMATION: rpe gene(NCgl1536)

<400> SEQUENCE: 3
atggcacaac gtactccact aatcgcccca tccattcttg ctgctgattt ctcccgctta     60
ggggagcagg tgttggctgt tcctgatgct gactggattc acgtcgacat catggacgga   120
cacttcgttc caaacttgag ctttggcgcg gatatcacag ctgcggtcaa ccgcgttacg   180
gacaaagaac tagacgtcca cctgatgatc gaaaacccag agaagtgggt ggacaactac   240
atcgacgctg gcgcggactg cattgttttc cacgttgaag ccaccgaagg tcacgttgag   300
ttggctaagt acatccgttc caagggtgtg cgtgcaggtt tctccctgcg ccctggaact   360
cccatcgagg attacttgga tgacctcgag cacttcgatg aagtcatcgt catgagcgtc   420
gagcctggat tcggtggcca aagcttcatg cctgaacaac tggaaaaggt tcgtaccctg   480
cgcaaggtca tcgatgagcg cggtctgaac accgtcatcg agatcgacgg cggcattagc   540
gccaagacca tcaagcaggc tgccgacgct ggcgtggatg ccttcgttgc aggttccgct   600
gtgtacggcg ctgaggatcc caacaaggcg atccaggagt tgcgagcact cgcgcagtaa   660

<210> SEQ ID NO 4
<211> LENGTH: 987
<212> TYPE: DNA
<213> ORGANISM: Corynebacterium glutamicum ATCC 13032
<220> FEATURE:
<221> NAME/KEY: gene
<222> LOCATION: (1)..(987)
<223> OTHER INFORMATION: ribG gene(NCgl1535)

<400> SEQUENCE: 4
atggatgttg cgcacgcgtt agatctggcc caccacgtgt cagatcaagt ccgaggcacc     60
accagcccta atccgccagt cggcgctgtc attttggacg ccgacggcga ggtcgttggc    120
gttggcgcca cggcacctcc tggtggcccg cacgccgaag tggtggcgct tgcagctgcc    180
```

```
ggagtgcgtg ccaacggggg cacggcggtg gtcaccctcg agccgtgcaa ccattacggc      240
cgcacgggtc catgttccaa ggcgcttctc gacgccggga tcgcacacgt gttttacgcc      300
aatgcggatc ccttcccgtc agccgctggg ggcggtgcct ttttggcgga ggcgggcgtc      360
gatacgcatt ttttagatga gcggatcagg gcactggagc cctggctggt tgcgacgcgt      420
ctgggcaggc cccatgtcac gttgaagttt gcgtccaccg tggacggttt tgctggtgcc      480
accgatggca ccagccagtg gattaccggg ccggatgcgc gggcgtttgt gcacgaagat      540
cgaagtaaaa gagatgcgat catcgtgggt accggtactg cgttgactga taatccctcc      600
ttgacggcgc ggaccgatac gggtctttat gaaaatcaac ccaggcgcgt tgttattggc      660
tcccgcgagg ttccagcaga ttccaacttg gctcgcttgg gatatgagca gtacgcggga      720
ataccagagg ctttatcagc gctgtgggat aaagggtgcc gagacatttt aatcgaaggt      780
ggcccaacgt tagctggggc agcgctgcgc ttaggcattg ttgatcaggt gcaggcctat      840 gttgccccccg ctttgttggg cgctggacga tcagtgatta actggccaca agaaaccacg      900
atggatcaga ttatgcgttt tgacaccacg tccgtgagac agttgggttc agatgtattg      960
atagaaatga tgagaaagga acactaa                                          987
```

```
<210> SEQ ID NO 5
<211> LENGTH: 250
<212> TYPE: DNA
<213> ORGANISM: Artificial Sequence
<220> FEATURE:
<223> OTHER INFORMATION: Pmrb promoter

<400> SEQUENCE: 5
gattgtgtac tccacatgtt cacctgatct gcgtgaaacc cgcggaatcg tggacaaggc       60 actggggggct ctggagatcg aagagcttga ggctgcggag ttcatgccag gcatgaccga     120
taccggcgat gagaaatcag tgcagatgtg gccacaccgc cacggcaccg atgcgatgtt     180
tgtggcagtg ctgcgaaaga agtagacctg tgagctaagt ggggtagaca agagtgctat     240
aatttagggc                                                             250
```

```
<210> SEQ ID NO 6
<211> LENGTH: 353
<212> TYPE: DNA
<213> ORGANISM: Artificial Sequence
<220> FEATURE:
<223> OTHER INFORMATION: lysCP1 promoter

<400> SEQUENCE: 6
ccatcttttg gggtgcggag cgcgatccgg tgtctgacca cggtgcccca tgcgattgtt       60
aatgccgatg ctagggcgaa aagcacggcg agcagattgc tttgcacttg attcagggta     120
gttgactaaa gagttgctcg cgaagtagca cctgtcactt ttgtctcaaa tattaaatcg     180
aatatcaata tatggtctgt ttattggaac gcgtcccagt ggctgagacg catccgctaa     240
agccccagga accctgtgca gaaagaaaac actcctctgg ctaggtagac acagtttatt     300
gtggtagagt tgagcgggta actgtcagca cgtagatcga aggtgcaca aag              353
```

```
<210> SEQ ID NO 7
<211> LENGTH: 28
<212> TYPE: DNA
<213> ORGANISM: Artificial Sequence
<220> FEATURE:
<223> OTHER INFORMATION: primer for Pmrb promoter

<400> SEQUENCE: 7
```

-continued

```
tttgaattcg tgtgcgtgca ggtttctc                                28
```

<210> SEQ ID NO 8
<211> LENGTH: 26
<212> TYPE: DNA
<213> ORGANISM: Artificial Sequence
<220> FEATURE:
<223> OTHER INFORMATION: primer for Pmrb promoter

<400> SEQUENCE: 8

```
tttgtcgaca ttccgctaaa acacgt                                  26
```

<210> SEQ ID NO 9
<211> LENGTH: 29
<212> TYPE: DNA
<213> ORGANISM: Artificial Sequence
<220> FEATURE:
<223> OTHER INFORMATION: primer for lysCP1 promoter

<400> SEQUENCE: 9

```
tttgaattcg tgtgcgtgca ggtttctcc                               29
```

<210> SEQ ID NO 10
<211> LENGTH: 25
<212> TYPE: DNA
<213> ORGANISM: Artificial Sequence
<220> FEATURE:
<223> OTHER INFORMATION: primer for lysCP1 promoter

<400> SEQUENCE: 10

```
tttctagatt actgcgcgag tgctc                                   25
```

<210> SEQ ID NO 11
<211> LENGTH: 33
<212> TYPE: DNA
<213> ORGANISM: Artificial Sequence
<220> FEATURE:
<223> OTHER INFORMATION: primer for lysCP1 promoter

<400> SEQUENCE: 11

```
ttttctagat aacatatgga tgttgcgcac gcg                          33
```

<210> SEQ ID NO 12
<211> LENGTH: 26
<212> TYPE: DNA
<213> ORGANISM: Artificial Sequence
<220> FEATURE:
<223> OTHER INFORMATION: primer for lysCP1 promoter

<400> SEQUENCE: 12

```
tttgtcgaca ttggcgtaaa acacgt                                  26
```

<210> SEQ ID NO 13
<211> LENGTH: 29
<212> TYPE: DNA
<213> ORGANISM: Artificial Sequence
<220> FEATURE:
<223> OTHER INFORMATION: primer for lysCP1 promoter

<400> SEQUENCE: 13

```
ttttctagat agggagccat cttttgggg                               29
```

<210> SEQ ID NO 14
<211> LENGTH: 25
<212> TYPE: DNA

```
<213> ORGANISM: Artificial Sequence
<220> FEATURE:
<223> OTHER INFORMATION: primer for lysCP1 promoter

<400> SEQUENCE: 14
tttcatatgc tttgtgcacc tttcg                                          25

<210> SEQ ID NO 15
<211> LENGTH: 29
<212> TYPE: DNA
<213> ORGANISM: Artificial Sequence
<220> FEATURE:
<223> OTHER INFORMATION: primer for rib operon

<400> SEQUENCE: 15
tttggtaccg attgaaaagt ccgtgcgtg                                      29

<210> SEQ ID NO 16
<211> LENGTH: 29
<212> TYPE: DNA
<213> ORGANISM: Artificial Sequence
<220> FEATURE:
<223> OTHER INFORMATION: primer for rib operon

<400> SEQUENCE: 16
tttggtaccc gcgatctttt tcagaaact                                      29

<210> SEQ ID NO 17
<211> LENGTH: 611
<212> TYPE: DNA
<213> ORGANISM: Corynebacterium glutamicum

<400> SEQUENCE: 17
ccatcttttg gggtgcggag cgcgatccgg tgtctgacca cggtgcccca tgcgattgtt     60
aatgccgatg ctagggcgaa agcacggcg agcagattgc tttgcacttg attcagggta    120
gttgactaaa gagttgctcg cgaagtagca cctgtcactt ttgtctcaaa tattaaatcg   180
aatatcaata tatggtctgt ttattggaac gcgtcccagt ggctgagacg catccgctaa   240
agccccagga accctgtgca gaaagaaaac actcctctgg ctaggtagac acagtttatt   300
gtggtagagt tgagcgggta actgtcagca cgtagatcga aaggtgcaca aaggtggccc   360
tggtcgtaca gaaatatggc ggttcctcgc ttgagagtgc ggaacgcatt agaaacgtcg   420
ctgaacggat cgttgccacc aagaaggctg gaaatgatgt cgtggttgtc tgctccgcaa   480
tgggagacac cacggatgaa cttctagaac ttgcagcggc agtgaatccc gttccgccag   540
ctcgtgaaat ggatatgctc ctgactgctg gtgagcgtat ttctaacgct ctcgtcgcca   600
tggctattga g                                                        611
```

MICROORGANISM FOR SIMULTANEOUSLY PRODUCING L-AMINO ACID AND RIBOFLAVIN, AND METHOD FOR PRODUCING L-AMINO ACID AND RIBOFLAVIN USING SAME

CROSS-REFERENCES TO RELATED APPLICATIONS

This application is a U.S. national phase application of International PCT Patent Application No. PCT/KR2012/008456, which was filed on Oct. 17, 2012, which claims priority to Korean Patent Application No. 10-2011-0127955, filed Dec. 1, 2011. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_029_00US_ST25.txt. The text file is 17 KB, was created on May 30, 2014, and is being submitted electronically via EFS-Web.

TECHNICAL FIELD

The present invention relates to a method for producing high concentrations of L-amino acid and riboflavin, and a microorganism for simultaneously producing L-amino acid and riboflavin.

BACKGROUND ART

Cereal grains, such as corn, Indian millet, barley and wheat, which are most frequently used in feed, usually provide 30-60% of the amino acid requirement. Thus, in order to satisfy the remaining requirements and maintain the balance between essential amino acids, additional provision of amino acids is required. Also, all feeds contain certain amounts of vitamins, and if any vitamin is not provided in a sufficient amount, a deficiency of the vitamin can be occurred. Thus, vitamins should additionally be provided to maintain their proper levels, like amino acids. Amino acids are the most expensive among feed components, and efficient provision of amino acids can be considered as one of factors that determines the overall ability to produce livestock. Particularly, L-lysine and L-threonine among amino acids frequently become the first amino acids that limit the growth of livestock. L-lysine and L-threonine may be produced by a fermentation process using microorganisms, and the L-lysine and L-threonine produced by the fermentation process are added to feed after purification and concentration. Microorganisms that are typically used in the fermentation of L-lysine are *Corynebacterium* sp. or *Escherichia coli*, and many examples that produced L-lysine by genetically engineering the microorganisms have been reported (Korean Patent No. 10-0930203 and No. 10-0924065, and U.S. Pat. No. 7,871,801).

Currently, efforts are being continuously made to increase the production of L-lysine or L-threonine by modified microorganisms using genetic engineering methods. However, with the growth of the industry, the ability to provide increased amounts of L-lysine or L-threonine is required, and thus efforts are being made to develop methods capable of producing L-lysine or L-threonine in a more effective and economical way.

Although vitamins are required in small amounts, they are essential organic compounds that must be provided for the maintenance of normal metabolic functions, growth, reproductive functions and health of livestock. Among vitamins, riboflavin (vitamin B2) is a water-soluble vitamin that is biosynthesized in various species of microorganisms and all kinds of plants, but it is not biosynthesized in the body of vertebrates, including humans, and thus is required to be provided by external sources. A deficiency of riboflavin can cause anestrus and reproductive failure in pigs (*Biol. Reprod*. (1981) 25:659-665, *J. Anim. Sci*. (1984) 59:1567-1572). In fowls, it can cause problems in nerves, particularly sciatic nerves and brachial nerves and can adversely affect the growth of embryos, resulting in the death of embryos (the Korean Feeding Standard for Poultry, 2002, the Korean Ministry of Agriculture and Forestry). Thus, riboflavin has been used as a feed additive for the growth of livestock, and particularly, concentrated riboflavin itself has been used as feed.

The current worldwide production of riboflavin is 6,000 tons per year, of which 75% is used as feed additives and the remainder is used as foods and pharmaceuticals. In riboflavin production, a chemical synthesis method and a microbial fermentation method are used. In a chemical synthesis method, high-purity riboflavin is produced from a precursor such as D-ribose by a multi-step process. The chemical synthesis method has a disadvantage in that the starting material is expensive and thereby increases the production cost. For this reason, a method of producing riboflavin by microbial fermentation was developed. The microbial fermentation method is a method in which either a microorganism that produces riboflavin is isolated from nature or a microorganism mutated by a genetic engineering method or a chemical/physical method so as to overproduce riboflavin is cultured under suitable conditions, and then riboflavin is isolated from the culture. In recent years, the fermentation method has been primarily researched, because it is price-competitive and environmentally friendly. Riboflavin produced by the fermentation method is added to feed after purification and concentration.

A typical method of producing riboflavin using the yeast *Candida famata* is disclosed in U.S. Pat. No. 5,231,007. In the industrial production of riboflavin, *Eremothecium ashbyii* and *Ashbya gossypii* (WO No. 95/26406), which are belong to Ascomycetes, are most frequently used. In addition, the bacterium *Bacillus subtilis* was also reported as a strain that can be used for producing riboflavin. Many examples that produced riboflavin by genetically engineering the above bacterium have been reported (EP No. 0821063, U.S. Pat. Nos. 5,837,528, and 5,334,510), and the present inventors also produced riboflavin using the above bacterium (Korean Patent No. 10-0542573). In addition, an example that produced 4.5 g/L of riboflavin using a microorganism engineered to overexpress a riboflavin biosynthesis-related enzyme gene was also reported (J. Ind. Microbiol. Biotechnol. (1999), 22:8-8).

The requirements for components in animal feed are about 1-5 g/kg of L-lysine, about 0.6-3.3 g/kg of L-threonine, and 2-4 mg/kg of riboflavin, which is about 0.1% of the requirement of L-lysine (NRC. 1998. National Academy of Sciences—National Research Council, Washington, D.C.). However, L-lysine and riboflavin are separately produced by fermentation processes, are subjected to purification and concentration processes before their addition to feed, and are individually transferred to a feed compounding plant. For this reason, they can increase the production cost of feed. If the concentration of riboflavin in a microorganism that produces both L-Lysine and riboflavin reaches about 0.1% of the concentration of L-lysine, addition of the microbial culture can satisfy the requirements for feed additives, but attempts to achieve this have not yet been reported.

In the case of *Corynebacterium* sp. microorganisms, riboflavin is biosynthesized through two pathways from ribulose 5-phosphate (Ru5P), which is a pentose-phosphate pathway (PPP) product, and guanosine triphosphate (GTP) that is a purine metabolism product. In the biosynthesis of riboflavin, a gene family consisting of GTP cyclohydrolase II (RibA) gene, pyrimidine deaminase-reductase (RibG) gene, riboflavin synthase subunit alpha (RibC) gene and riboflavin synthase subunit beta (RibH) gene (hereinafter referred to as "riboflavin biosynthesis gene family") is involved. The riboflavin biosynthesis gene family forms an operon (rib operon) with ribulose-5-phosphate-3-epimerase (Rpe, NCgl1536) that is involved in the pentose-phosphate pathway, and both the Rpe and the RibA compete in the use of Ru5P as a substrate (FIG. 1). In other words, Rpe biosynthesizes D-xylose-5-phosphate from Ru5P to mediate an intermediate process in which a metabolic product produced in the pentose-phosphate pathway enters the glycolytic pathway, and RibA biosynthesizes 3,4-dihydroxy-2-butanone-4-phosphate that is an intermediate of riboflavin biosynthesis (KEGG, Kyoto Encyclopedia of Genes and Genomes, [at the world wide web address: genome.jp/kegg]).

The pentose-phosphate pathway in *Corynebacterium* is the major source of reducing power (NADPH) that is involved in lysine biosynthesis, and the direct correlation between the regeneration of NADPH and L-lysine biosynthesis has been reported in the literature (Wittmann and Heinzle, Microbiol 68:5843-5849, 2002; Marx et al., J Biotechnol 104:185-197, 2003; Ohnishi et al., Microbiol Lett 242:265-274, 2005).

The pentose-phosphate pathway is catalyzed by glucose-6-phosphate dehydrogenase (G6PDH), 6-phosphogluconolactonase, 6-phosphogluconate dehydrogenase (6PGD), Rpe, ribose-5-phosphate isomerase (RpiA), transketolase and transaldolase, and the final metabolic product produced by this pathway enters the glycolytic process.

As a result of studies on the enforcement of the pentose-phosphate pathway, EP 01941065 (June, 2001) and EP 02781875 (December, 2002) disclose an enzyme variant which directly produce NADPH, which has negative feedback resistance. In addition, inventions relating to lysine-producing *Corynebacterium* strains that overexpress transketolase and transaldolase were disclosed (EP 1109915, EP 1179076, and EP 1179084). Moreover, an increase in the production of L-lysine in a *Corynebacterium* strain that overexpresses Rpe or RpiA was reported (DE10037611 and DE10037612).

Thus, it can be seen that as the production of L-lysine in a *Corynebacterium* strain increases, the dependence of the strain on the pentose-phosphate pathway increases. However, the riboflavin biosynthesis pathway that is the key element of the present invention is derived from the pentose-phosphate pathway, and thus if a carbon flow to the riboflavin biosynthesis pathway is enhanced, a carbon source to be introduced into the glycolytic pathway through the pentose-phosphate pathway will leak, resulting in a decrease in the L-lysine production yield per unit of carbon source supplied. In other words, it can be considered that the riboflavin biosynthesis pathway in an L-lysine-producing strain that requires a sufficient carbon flow in the pentose-phosphate pathway is competitive with the pentose-phosphate pathway. Also, if a carbon flow that is introduced into the riboflavin biosynthesis pathway increases, the production of L-lysine can be adversely affected.

Thus, microorganisms that simultaneously produce L-lysine and riboflavin can be present in nature, but the production yields of L-lysine and riboflavin can be competitive with each other. For this reason, attempts to increase the production of riboflavin in an industrial microorganism, which produces a large amount of L-lysine, to an industrially useful level, have not yet been reported.

DISCLOSURE

Technical Problem

Under above circumstances, the present inventors have made extensive efforts to develop a microorganism that simultaneously produces L-lysine and riboflavin. As a result, the present inventors have imparted high-concentration gluconic acid adaptability into a *Corynebacterium* strain having L-lysine-producing ability by artificial mutation in order to increase carbon flow in the pentose-phosphate pathway, thereby developing a mutant strain that has an increased ability to produce riboflavin compared to the parent strain while maintaining the production of L-lysine at a similar level to that of the parent strain. Also, the present inventors have found that, even when the promoter of the riboflavin biosynthesis gene family in an L-lysine-producing *Corynebacterium* strain is replaced with a heterogeneous strong promoter, the *Corynebacterium* strain can simultaneously produce L-lysine and riboflavin at high concentrations, and the same effect also appears in a *Corynebacterium* strain having L-threonine-producing ability, thereby completing the present invention.

Technical Solution

It is an object of the present invention to provide a method for producing L-lysine or L-threonine, and riboflavin, comprising: culturing a microorganism which is obtained by modifying a *Corynebacterium* sp. microorganism having L-lysine or L-threonine-producing ability so as to increase the production of riboflavin while maintaining the production of L-lysine or L-threonine at a high level; and producing L-lysine or L-threonine, and riboflavin by a fermentation process.

Another object of the present invention is to provide a modified *Corynebacterium glutamicum* microorganism which is obtained by inducing a random mutation in a *Corynebacterium glutamicum* microorganism having high-concentration L-lysine-producing ability so as to increase the production of riboflavin while maintaining the production of L-lysine at a high level, wherein the modified *Corynebacterium glutamicum* microorganism is deposited under accession No. KCCM11223P.

Still another object of the present invention is to provide a modified *Corynebacterium* sp. microorganism for simultaneously producing L-lysine or L-threonine, and riboflavin, which is modified by enhancing activity of an enzyme family that is expressed by the rib operon comprising riboflavin biosynthesis gene family in a *Corynebacterium* sp. microorganism having L-lysine or L-threonine-producing ability so as to increase the production of riboflavin while maintaining the production of L-lysine or L-threonine at a high level.

Still another object of the present invention is to provide a formulation or granular formulation comprising L-amino acid and riboflavin, which is prepared by culturing the above-described microorganism and granulating L-amino acid and riboflavin.

Still another object of the present invention is to provide a feed additive comprising a formulation comprising L-amino acid and riboflavin, which is prepared by culturing the above-described microorganism, or the above-described granular formulation.

Advantageous Effects

The present invention can provide a developed microorganism that can simultaneously produce high concentrations of L-amino acid, such as L-lysine or L-threonine which is industrially produced in large amounts, and riboflavin, which are used as essential animal feed, and the method for producing L-amino acid and riboflavin. Thus, the present invention can provide the effects of manufacturing feeds conveniently and reducing the production cost and can provide an efficient strain for producing L-amino acid and vitamin feed additives.

BEST MODE

Hereinafter, the terms used herein will be defined.

Figure 1:
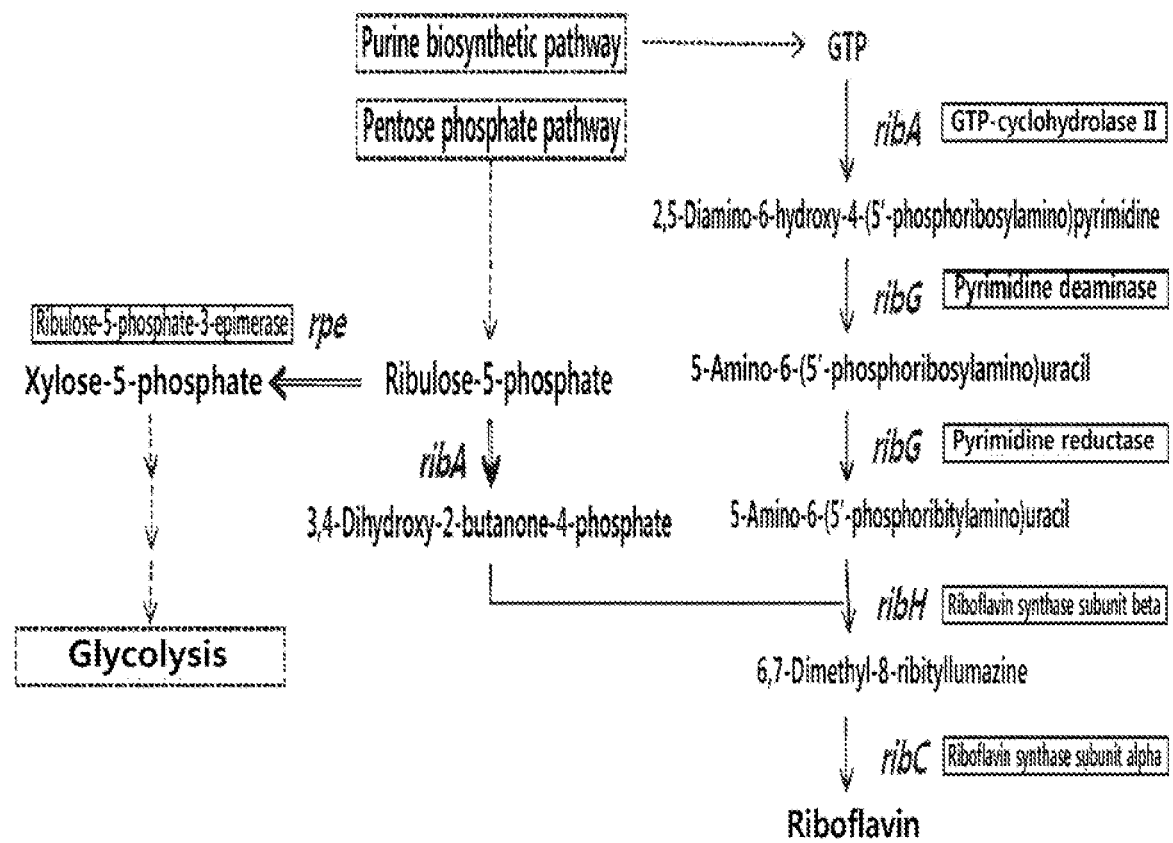
FIG. 1 shows that the glycolytic pathway and the riboflavin biosynthesis pathway compete in the use of ribulose-5-phosphate.
Figure 2:
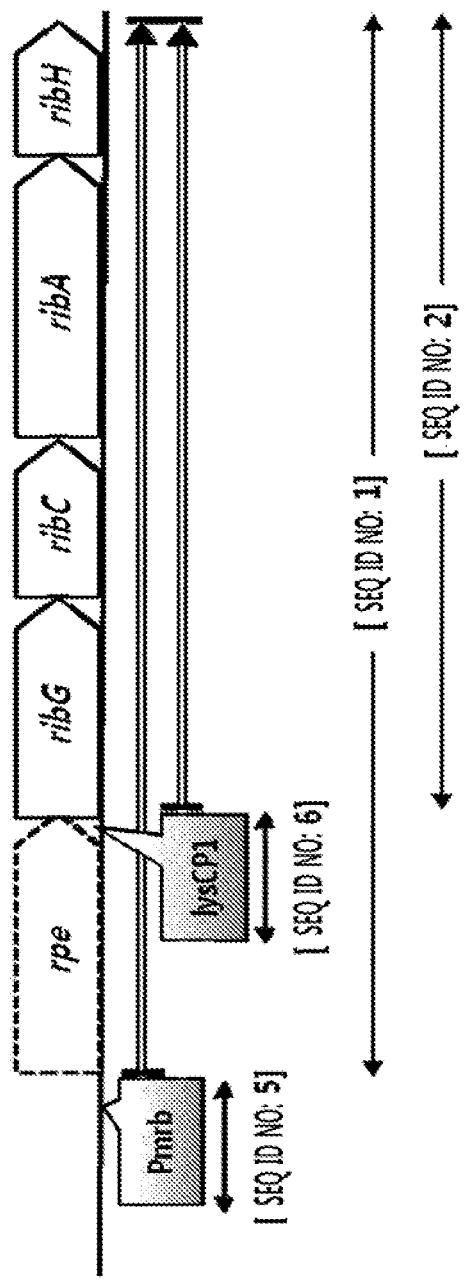
FIG. 2 shows that a strong promoter is inserted to the upstream or inside of the rib operon to enhance the activity of either the enzyme family that is encoded by the rib operon or the riboflavin biosynthesis enzyme family.

As used herein, the term "rib operon" refers to an operon including a riboflavin biosynthesis gene family consisting of ribG gene encoding pyrimidine deaminase-reductase (RibG, NCgl1535), ribC gene encoding riboflavin synthase subunit alpha (RibC, NCgl1534), ribA gene encoding GTP cyclohydrolase II (RibA), and ribH gene encoding riboflavin synthase subunit beta (RibH, NCgl1532) (hereinafter referred to as "riboflavin biosynthesis gene family"), and rpe gene encoding ribulose-5-phosphate-3-epimerase (Rpe, NCgl1536) that is involved in the pentose-phosphate pathway (FIG. 2). Information on the genes of the operon is available from public databases (e.g., NCBI GenBank).

As used herein, the term "L-amino acid" refers to an amino acid selected from the group consisting of L-lysine, L-threonine, L-valine, L-isoleucine, L-tryptophan and L-methionine. Specifically, the amino acid is L-lysine or L-threonine.

One aspect of the present invention contains a method for producing L-lysine or L-threonine, and riboflavin, comprising:

culturing a microorganism which is obtained by modifying a *Corynebacterium* sp. microorganism having L-lysine or L-threonine-producing ability so as to increase the production of riboflavin while maintaining the production of L-lysine or L-threonine at a high level; and producing L-lysine or L-threonine, and riboflavin by a fermentation process.

In a specific example of the present invention, it was found that the production of L-lysine or L-threonine in the modified microorganism was maintained at the same level as that of the parent strain while the production of riboflavin increased by about 70-80 times, and particularly the ratio between the production of lysine and the production of riboflavin was about 1:0.005 or the ratio between the production of L-threonine and the production of riboflavin was about 1:0.03 (Tables 1 to 6). This suggests that L-amino acid and riboflavin simultaneously produced by the microorganism of the present invention are suitable for use as feed additives.

The modified microorganism is modified *Corynebacterium* sp. microorganism for simultaneously producing L-amino acid and riboflavin, which is obtained by modifying a *Corynebacterium* sp. microorganism having L-amino acid-producing ability so as to increase the production of riboflavin while maintaining the production of L-amino acid, as a result of enhancing the activity of an enzyme family that is expressed by the rib operon including the riboflavin biosynthesis gene family. Specifically, it may be a mutant *Corynebacterium* sp. microorganism for simultaneously producing L-lysine or L-threonine and riboflavin, which is obtained by modifying a *Corynebacterium* sp. microorganism having L-lysine or L-threonine-producing ability so as to increase the production of riboflavin while maintaining the production of L-lysine or L-threonine, as a result of enhancing the activity of an enzyme family that is expressed by the rib operon including the riboflavin biosynthesis gene family.

The *Corynebacterium* sp. microorganism used in the present invention may be any *Corynebacterium* sp. strain having the ability of producing L-amino acid, and examples thereof include, but are not limited to, *Corynebacterium glutamicum* (ATCC 13032), *Corynebacterium ammoniagenes*, *Corynebacterium thermoaminogenes* (FERM BP-1539), *Brevibacterium flavum* (ATCC 14067), and *Brevibacterium fermentum* (ATCC 13869). More specifically, *Corynebacterium glutamicum* may be used, and specific examples thereof include, but are not limited to, KFCC10881 (Korean Patent No. 0159812), KFCC11074 (Korean Patent No. 0292299), KFCC11001 (Korean Patent No. 0253424) and KCCM11222P. In a specific example of the present invention, a mutant microorganism was produced by modifying KFCC10881 as a parent strain to increase the production of riboflavin while maintaining the production of L-lysine or L-threonine at a high level. Particularly, a mutant microorganism was produced by modifying KCCM11222P as a parent strain to increase the production of riboflavin while maintaining the production of L-threonine at a high level.

The *Corynebacterium* sp. microorganism having the ability of producing L-lysine may be a microorganism that produces L-lysine with increased efficiency. Methods for increasing the production efficiency of L-lysine include a method of amplifying a gene that is involved in the L-lysine biosynthesis pathway or modifying the promoter of the gene to increase the enzymatic activity. Examples of enzymes involved in L-lysine biosynthesis include aspartate aminotransferase, aspartokinase, aspartate semialdehyde dehydrogenase, pyruvate carboxylase, dihydrodipicolate reductase, dihydrodipicolinate synthase, diaminopimelate decarboxylase, and the like. Previous patent related to Coryne-type bacterium-derived promoters includes WO09/096690 relating to the improved promoter of dihydrodipicolinate reductase, and Korean Granted Patent No. 0930203 discloses the improved promoters of aspartokinase and aspartate semialdehyde dehydrogenase. Also, Korean Granted Patent No. 0924065 discloses a method of improving the production of L-lysine by introducing one or more copies of the above-mentioned biosynthesis-related genes and replacing the promoters of the genes with exogenous strong promoters.

The *Corynebacterium* sp. microorganism having the ability to produce L-threonine may be a microorganism that produces L-threonine with increased efficiency. In order to improve the ability to produce L-threonine, conventional methods can be used by those skilled in the art such as not only the acquisition of auxotrophic mutants, analogue resistant mutants, metabolism regulatory mutants, but also the construction of recombinant strains having increased activity of L-threonine biosynthetic enzyme. For example, a mutant strain or a recombinant strain can be modified so that the L-threonine biosynthetic enzyme does not undergo feedback inhibition, or a recombinant strain can be modified to increase the expression of L-threonine biosynthetic enzyme gene. In the modification of the L-threonine-producing strain by these methods, properties such as auxotrophy, analogue resistance and metabolism regulatory mutations can be provided alone or in combination. If the activity of L-threonine biosynthetic enzyme is enhanced, the activity of one or more of these enzymes can be enhanced. Examples of the gene encoding L-threonine biosynthetic enzyme include aspartokinase III gene (lysC), aspartate semialdehyde dehydrogenase gene (asd), aspartokinase I gene (thrA), homoserine kinase gene (thrB) and threonine synthase gene (thrC) which are included in the thr operon. The activity of L-threonine biosynthetic enzyme can be increased by introducing a mutation into the gene encoding the enzyme or amplifying the gene to increase the intracellular activity of the enzyme. These can be achieved using genetic recombination technology. Also, the production of L-threonine can be increased by deleting L-threonine dehydrogenase activity related to threonine degradation. In addition to the enzymes of the L-threonine degradation system, the production of L-threonine can be increased by reducing or deleting enzymes that are involved in the glycolytic pathway, the TCA cycle or the respiratory chain process, which adversely affect the production of L-threonine, enzymes that regulate the expression of genes, or the enzymes of the byproduct biosynthetic system. Examples of a method for improving the efficiency of production of L-threonine include a method of modifying a microorganism to enhance the expression of enzymes that are involved in the L-threonine biosynthesis pathway. Enzymes that are involved in L-threonine biosynthesis include homoserine dehydrogenase, homoserine kinase, threonine synthase, and threonine exporter. Other examples of a method for imparting or enhancing the ability to produce L-threonine include a method of introducing a mutation to make homoserine dehydrogenase resistant to feedback by threonine (U.S. Pat. No. 6,649,379). In a specific example of the present invention, mutant microorganism KFCC10881-THR (accession number: KCCM11222P) was produced by modifying KFCC10881 to have resistance to the L-threonine analogue AHV (2-amino-3-hydroxy-valerate).

Specifically, the modified *Corynebacterium* sp. microorganism may be a modified *Corynebacterium* sp. microorganism for producing high concentrations of L-amino acid and riboflavin, which is obtained by modifying a *Corynebacterium* sp. microorganism having high L-amino acid-producing ability so as to increase the production of riboflavin while maintaining the production of L-amino acid at a high level, as a result of enhancing the activity of enzymes that are expressed by the rib operon. Furthermore, it may be a microorganism obtained by enhancing the activity of the enzyme that is expressed by the riboflavin biosynthesis gene family of the rib operon.

The method of enhancing the activity of the enzyme may be, for example, one or more selected from the group consisting of a method of increasing the intracellular copy number of a gene encoding each enzyme of the "operon or enzyme family" (hereinafter referred to as "enzyme family"), a method of introducing a mutation into an expression regulatory sequence for the chromosomal gene encoding each enzyme of the enzyme family, a method of replacing the expression regulatory sequence for the chromosomal gene encoding each enzyme of the enzyme family with a sequence having strong activity, a method of substituting the chromosomal gene encoding the enzyme with a gene mutated to increase the activity of the enzyme family, and a method of introducing a mutation into the chromosomal gene encoding each enzyme of the enzyme family to enhance the activity of the gene family, but is not limited thereto. This method can be performed by various methods known in the art. Specifically, the method may be a method of replacing the regulatory sequence for the chromosomal gene encoding the enzyme family, which is expressed by the rib operon, with a strong promoter, a method of inserting a strong promoter to upstream of the chromosomal gene encoding RibG (pyrimidine deaminase-reductase) located in the front of the riboflavin biosynthesis gene family, or a method of increasing the intracellular copy number of the gene encoding either the enzyme family that are expressed by the rib operon or the enzyme family that is expressed by the riboflavin biosynthesis gene family.

The expression "increasing the intracellular copy number" may include the case in which the enzyme-encoding gene is operably linked into the chromosome to stably express the enzyme or the case in which a vector comprising the enzyme-encoding gene is operably transformed into the chromosome to stably express the enzyme. As used herein, the term "vector" refers to a DNA construct containing the nucleotide sequence of a gene operably linked to a suitable regulatory sequence so as to express the target gene in a suitable host cell.

Based on the results obtained by increasing the copy number of the gene encoding the enzyme that is expressed by rib operon in the chromosomal DNA, any person skilled in the art could appreciate that an increase in the copy number of the gene encoding the enzyme that is expressed by the rib operon outside the chromosome by a vector, a modification of the regulatory region of the gene encoding the enzyme that is expressed by the rib operon inside or outside the chromosome or a modification of the gene itself to increase expression would achieve the same result.

When a vector is used, it is possible to prepare a microorganism having enhanced activity of the enzyme that is expressed by the rib operon, by transforming a *Corynebacterium* sp. microorganism having L-amino acid-producing ability with a recombinant vector having a nucleotide sequence introduced therein. The vector that may be used in the present invention is not specifically limited, and a known vector may be used in the present invention. Examples of vectors that may be used in the present invention include pACYC177, pACYC184, pCL, pECCG117, pUC19, pBR322 and pMW118 vectors. In a specific example of the present invention, pECCG117 was used.

In prokaryotes, the regulatory sequence includes a promoter capable of initiating transcription, any operator for regulating this transcription, a suitable ribosome binding site (RBS) encoding a suitable mRNA ribosome binding site, a sequence for regulating the termination of transcription, and a sequence for regulating the termination of translation.

In place of the inherent promoter located upstream of the gene encoding the enzyme, an improved promoter having a nucleotide substitution mutation, generated from the inherent promoter or heterogeneous promoter, can be used. Examples of the heterogeneous promoter include pcj7 promoter, lysCP1 promoter, EF-Tu promoter, groEL promoter, aceA promoter, aceB promoter and the like. Specifically, pcj7 promoter or lysCP1 promoter from *Corynebacterium* may be used. Most specifically, lysCP1 promoter may be used.

As used herein, the term "lysCP1 promoter" means a promoter improved by nucleotide substitution of a promoter region of the gene encoding aspartate kinase and aspartate semialdehyde dehydrogenase, and a strong promoter that increases the expression level of aspartate kinase gene to improve the enzymatic activity to be approximately 5 times more than that of the wild-type (WO 2009/096689). The lysCP1 promoter can be nucleotide residues 1 to 353 (SEQ ID NO: 6) of SEQ ID NO: 17, which comprise the lysCP1 promoter sequence and the part of lysC-asd gene. Specifically, the vector was constructed such that an improved promoter of SEQ ID NO: 5 comprising a nucleotide substitution mutation or the improved promoter of lyc C gene, lysCP1 of SEQ ID NO: 6, having strong expression-inducing activity can be introduced into the chromosome of the host cell. Methods for overexpressing the target gene include a method of improving a promoter by substituting some nucleotides of the inherent promoter sequence with other nucleotides to increase the expression level, or a method of substituting a promoter with the promoter of another gene having a high expression level (WO 2009/096689).

As used herein, the term "transformation" means an overall action of introducing a gene into the host cell, *Corynebacterium* sp. for its expression in the host cell. In this regard, the promoter and the gene are polynucleotides, including DNA and RNA. As long as the gene can be introduced in the host cell and expressed therein, any type of the gene can be used. For example, the gene can be introduced into the host cell in a form of an expression cassette which is a polynucleotide construct including all elements for expressing the gene. The expression cassette includes a promoter which is operably linked to the gene, a transcription termination signal, a RBS, and a translation termination signal. The expression cassette may be a form of an expression vector capable of self-replication. The gene also may be introduced into the host cell by itself or in a polynucleotide construct to be operably linked to the sequence necessary for expression in the host cell.

Methods for transforming the vector of the present invention include any method for introducing nucleic acid into a cell, and a suitable standard transformation technique known in the art can be selected depending on a host cell. Examples of the transformation method include electroporation, calcium phosphate ($CaPO_4$) precipitation, calcium chloride ($CaCl_2$) precipitation, microinjection, a polyethylene glycol (PEG) method, a DEAE-dextran method, a cation liposome method, a lithium acetate-DMSO method and the like.

The host cell in the present invention can be a host in which DNA is introduced with high efficiency and expressed with high efficiency. Specifically, the *Corynebacterium* sp. microorganism as described above may be used. More specifically, *Corynebacterium glutamicum*, particularly *Corynebacterium glutamicum* KECC10881, may be used. As the microorganism having L-threonine-producing ability, any microorganism capable of producing L-threonine can be used without limitation. Specifically, KFCC10881-THR (accession number: KCCM11222P) may be used.

Specifically, the microorganism can be obtained by replacing the promoter located in the upstream of the chromosomal region, which encodes the enzyme family that is expressed by the rib operon, with the promoter of SEQ ID NO: 5, or replacing the upstream promoter of ribG gene with the promoter of SEQ ID NO: 6. In a specific example of the present invention, the promoter of KFCC10881 strain was replaced with the promoter of SEQ ID NO: 5, and as a result, it was shown that the average concentration of L-lysine did not change, but the average concentration of riboflavin increased by about 61 times (Table 2). Also, it was found that, when the upstream promoter of the ribG gene was replaced with the promoter of SEQ ID NO: 6, the average concentration of riboflavin increased by about 73 times (Table 3), and when the copy number of the rib operon was increased, the average concentration of riboflavin increased by 66 times (Table 4). In addition, it was shown that, when the promoter of L-threonine-producing strain KFCC10881-THR was replaced with the promoter of SEQ ID NO: 5 or 6, the average concentration of L-threonine rarely changed, but the concentrations of riboflavin increased by 56 times and 66 times, respectively (Table 6).

Specifically, a *Corynebacterium* sp. microorganism having the ability to produce L-lysine or L-threonine can be modified to produce a high concentration of riboflavin together with a high concentration of L-lysine or L-threonine, by inserting a strong promoter in the front of the gene encoding Rpe (ribulose-5-phosphate-3-epimerase) located upstream of the rib operon, or inserting a strong promoter into upstream of the gene encoding the RibG (pyrimidine deaminase-reductase) located in the front of the riboflavin biosynthesis gene family (FIG. 2), to enhancing of the activity of the enzyme family encoded by rib operon or riboflavin biosynthesis gene family. In a specific example of the present invention, it was found that there was a mutation in a nucleotide sequence of $-10^{th}$ to $-16^{th}$ nucleotide residues of the nucleotide sequence of rpe located upstream of rib operon of the KCCM11223P strain. Thus, the expected promoter region (SEQ ID NO: 5) of the rib operon of the KCCM11223P strain was cloned and then introduced into the chromosome of a parent strain having the ability to produce L-lysine, and as a result, it was found that the production of riboflavin in the strain increased to a similar level to that in the KCCM11223P strain while the production of L-lysine was maintained (Table 2). Accordingly, it was predicted that the production of riboflavin would be increased by the enhancement of the rib operon, and a strong promoter was introduced to upstream of ribG located in the front of the riboflavin biosynthesis gene family in the rib operon, and as a result, it was shown that the production of riboflavin in the modified strain increased by about 73 times compared to that in the parent strain (Table 3). In addition, it was found that, even when the copy number of the rib operon was increased, the production of riboflavin increased to a level similar to that in the use of the strong promoter (Table 4). Furthermore, when the promoter upstream of rpe in the parent strain having L-threonine-producing ability was replaced with the promoter of SEQ ID NO: 5 according to the present invention and when a strong promoter was introduced to upstream of ribG, it was found that the production of riboflavin increased by about 60-70 times while the production of L-threonine was maintained at a level similar to that in the parent strain (Table 6). Thus, it was found that the inventive *Corynebacterium* sp. microorganism obtained by modifying the parent strain to increase the production of riboflavin while maintaining the production of amino acid at a high level can produce high concentrations of L-amino acid and riboflavin at the same time.

Specifically, the modified *Corynebacterium* sp. microorganism that simultaneously produces L-lysine and riboflavin may be a *Corynebacterium glutamicum* (accession number: KCCM11223P) modified by inducing a random mutation in a *Corynebacterium glutamicum* having high L-lysine-producing ability so as to increase the production of riboflavin while maintaining the production of L-lysine at a high level. Furthermore, it may be a modified *Corynebacterium glutamicum* (accession number: KCCM11220P, KCCM11221P or KCCM11223P) obtained by modifying the *Corynebacterium* sp. microorganism having L-lysine-producing ability so as to increase the production of riboflavin while maintaining the production of L-lysine at a high level, as a result of enhancing the activity of the enzyme family that is expressed by the rib operon comprising the riboflavin biosynthesis gene family.

Performing random mutagenesis to increase carbon flow in the pentose-phosphate pathway of the L-lysine-producing strain, the present inventors found a microbial colony having a deep yellow color, and have found that the production of riboflavin in the mutant microorganism increased by about 60 times while the production of L-lysine was maintained at a level similar to that in the parent strain (Table 1). The present inventors have determined that this characteristic of the mutant strain is useful in the production of feed additives that should contain amino acid and riboflavin at a constant ratio. Accordingly, the mutant strain according to the present invention was named "*Corynebacterium glutamicum* CA01-2183" or "KFCC10881-YC" and deposited with the Korean Culture Center of Microorganisms (Yurim B/D, Honje 1-dong, Sudaemun-gu, Seoul, Korea) on Nov. 11, 2011 under the accession number KCCM11223P. In addition, the mutant strain obtained by introducing the Pmrb promoter into the rib operon promoter of the parent strain KFCC10881 was named "*Corynebacterium glutamicum* CA01-2162" or "KFCC10881::Pmrb" and deposited with the Korean Culture Center of Microorganisms (Yurim B/D, Honje 1-dong, Sudaemun-gu, Seoul, Korea) on Nov. 11, 2011 under the accession number KCCM11221P. In addition, the strain obtained by introducing lysCP1 upstream of the initiation codon of the ribG gene of the parent strain KFCC10881 was named "*Corynebacterium glutamicum* CA01-2161" or "KFCC10881::lysCP1_ribG". It was deposited with the Korean Culture Center of Microorganisms (Yurim B/D, Honje 1-dong, Sudaemun-gu, Seoul, Korea) on Nov. 11, 2011 under the accession number KCCM11220P.

The ratio of L-amino acid and riboflavin in the fermented culture medium, simultaneously produced by the method of the present invention, is 1:0.0001-0.1. If the L-amino acid is L-lysine, the ratio of L-lysine and riboflavin is specifically 1:0.001-0.05, and more specifically 1:0.003-0.01. If the L-amino acid is L-threonine, the ratio of L-threonine and riboflavin is specifically 1:0.001-0.1, and more specifically 1:0.005-0.05.

Culture of the *Corynebacterium* sp. microorganism can be performed in a suitable medium by various culture methods known in the art (Chmiel, Bipprozesstechnik 1. Einfuhrung in die Bioverfahrenstechnik, Gustav Fischer Verlag, Stuttgart, 1991; Storhas, Bioreaktoren und periphere Einrichtungen, Vieweg Verlag, Braunschweig/Wiesbaden, 1994). Examples of the culture method include batch culture, fed-batch culture, and continuous culture. Examples of the fed-batch culture include fed-batch culture and repeated fed-batch culture, but are not limited thereto.

In addition, a medium that may be used in culture in the present invention may be a suitable medium known in the art depending on the culture method and strain selected ("Manual of Methods for General Bacteriology" by the American Society for Bacteriology, Washington D.C., USA, 1981). The medium that is used in the present invention may contain various carbon sources, nitrogen sources and trace elements. The medium for culture of *Corynebacterium* microorganisms may contain, as carbon sources, sucrose, glucose, fructose, fat, fatty acid, alcohol, organic acid and the like. Specific examples of carbon sources that may be used in the present inventions include carbohydrates such as molasses, glucose, lactose, fructose, maltose, starch and cellulose, oils and fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources can be used in a suitable amount. Examples of nitrogen sources that may be used in the present invention include organic nitrogen sources such as peptone, yeast extract, meat juice, malt extract, corn steep liquor, and soybean cake hydrolysates, and inorganic nitrogen sources such as urea, ammonium sulfate, ammonium chloride, ammonium phosphate, ammonium carbonate and ammonium nitrate. These nitrogen sources may be used alone or in combination. The medium may contain, as phosphorus sources, potassium phosphate monobasic, potassium phosphate dibasic and corresponding sodium-containing salts. The medium may contain metal salts such as magnesium sulfate or iron sulfate. In addition, the medium may contain amino acids, vitamins and suitable precursors. These sources or precursors may be added to the medium in a batch or continuous manner.

Compounds such as ammonium hydroxide, potassium hydroxide, ammonia, phosphoric acid and sulfuric acid may be added to the medium in a suitable manner during culturing to adjust the pH of the culture medium. In addition, during culturing, a defoaming agent such as fatty acid polyglycol ester may be used to suppress the formation of foam. Further, in order to maintain the culture medium in an aerobic state, oxygen or oxygen-containing gas (e.g., air) can be injected into the culture medium. The culture medium can typically be maintained at a temperature ranging from 20° C. to 45° C., and specifically from 25° C. to 40° C. As for the culture period, culture can be continued until the desired level of L-amino acid will be obtained. Specifically, the culture period can be 10-160 hours.

The method of the present invention may further comprise a step of granulating the fermented culture medium comprising L-amino acid and riboflavin. The fermented culture medium may contain a bacterial sludge or may be free of the bacterial sludge. To remove the bacterial sludge, the method may further comprise a step of removing the bacterial sludge from the fermented culture medium containing L-threonine and riboflavin.

If the fermented culture medium contains bacterial sludge, a granular formulation can be produced, which does not require a filtration operation for removing the bacterial sludge and has a low moisture-absorbing property even when a moisture absorption preventing agent is not added thereto. Also, the granular formulation has good flowability and high apparent density, and the amino acid content thereof can be controlled. The granulation method can be performed using the method described in, for example, Korean Patent Registration No. 0838200 or No. 0338578. Specifically, the granulation method may comprise the step of: concentrating the fermentation broth; adding an excipient to the concentrate to form a mixed concentrate; introducing particulate seeds having a size of 200-500 μm into a granulation machine; and spraying the mixed concentrate from the bottom of the granulation machine while adding hot air to coat the particulate seeds with the concentrate while forming granules, but is not limited thereto.

If the fermentation broth contains no bacterial sludge, the granulation method may comprise the step of: filtering the fermented culture medium to remove the bacterial sludge; concentrating the filtrate; drying the concentrate to form granules; and coating the granules with a coating agent such as an excipient or a moisture absorption-preventing agent, but is not limited thereto.

The bacterial sludge can be removed from the fermented culture medium by separating L-amino acid and riboflavin using methods such as centrifugation, filtration, ion-exchange chromatography and crystallization. Specifically, L-amino acid and riboflavin can be separated by centrifuging the fermented culture medium at low speed to remove the bacterial sludge and separating the supernatant by ion exchange chromatography, but are not limited thereto.

In another aspect, the present invention provides a modified *Corynebacterium glutamicum* microorganism which is obtained by inducing a random mutation in a *Corynebacterium glutamicum* microorganism having high-concentration L-lysine-producing ability so as to increase the production of riboflavin while maintaining the production of L-lysine at a high level, wherein the modified *Corynebacterium glutamicum* microorganism is deposited under accession No. KCCM11223P.

Herein, the microorganism is as described above.

In still another aspect, the present invention provides a modified *Corynebacterium* sp. microorganism for producing L-lysine or L-threonine, and riboflavin, which is obtained by enhancing activity of an enzyme family that is expressed by the rib operon comprising riboflavin biosynthesis gene family in a *Corynebacterium* sp. microorganism having L-lysine or L-threonine-producing ability so as to increase the production of riboflavin while maintaining the production of L-lysine or L-threonine at a high level.

Herein, the microorganism, the enhancement of the enzyme family, and the modified *Corynebacterium* sp. microorganism are as described above.

In still another aspect, the present invention provides a granular formulation prepared by a method comprising: a) culturing a microorganism which is obtained by modifying a *Corynebacterium* sp. microorganism having L-lysine or L-threonine-producing ability so as to increase the production of riboflavin while maintaining the production of L-lysine or L-threonine at a high level, and producing L-lysine or L-threonine, and riboflavin by a fermentation process; and b) granulating the fermented culture medium of step a), which comprises L-lysine or L-threonine, and riboflavin.

Specifically, the L-amino acid may be L-lysine or L-threonine. The modified microorganism is as described above.

The method for preparing the granular formulation may further comprise a step of removing a bacterial sludge from the fermented culture medium of step a), which comprises L-lysine or L-threonine, and riboflavin. In other words, as described above, the granular formulation of the present invention may contain or not contain the bacterial sludge.

Specifically, the ratio of L-lysine or L-threonine:riboflavin in the granular formulation may be 1:0.0001-0.01 as described above.

As used herein, the term "granular formulation" means a granule-type formulation that overcomes the disadvantages of conventional power formulations, such as dust generation and product loss.

In still another aspect, the present invention provides a formulation comprising L-lysine or L-threonine, and riboflavin, the formulation is prepared by a method comprising: a) culturing a microorganism which is obtained by modifying a *Corynebacterium* sp. microorganism having L-lysine or L-threonine-producing ability so as to increase the production of riboflavin while maintaining the production of L-lysine or L-threonine at a high level, and producing L-lysine or L-threonine, and riboflavin by a fermentation process; and b) removing a bacterial sludge from the fermented culture medium of step a), which comprises L-lysine or L-threonine, and riboflavin.

Specifically, the ratio of L-lysine or L-threonine:riboflavin in the formulation may be 1:0.0001-0.01 as described above.

In still another aspect, the present invention provides a feed or a feed additive, which comprises the above-described granular formulation or the formulation comprising L-lysine, L-threonine and riboflavin.

In high concentrations of L-lysine or L-threonine, and riboflavin produced in a specific example of the present invention, the ratio of lysine:riboflavin was about 1:0.005, or the ratio of L-threonine:riboflavin was about 1:0.03 (see Tables 1 to 6). The requirements of components in animal feed are about 1-5 g/kg for L-lysine, about 0.6-3.3 g/kg for L-threonine, and 2-4 mg/kg for riboflavin, which is about 0.1% of the requirement of L-lysine (NRC. 1998. National Academy of Sciences—National Research Council, Washington, D.C.), and toxicity by administration of large amounts of L-lysine or L-threonine and riboflavin was not reported. Thus, it was found that L-amino acid and riboflavin, simultaneously produced by the method of the present invention are suitable for use as feed additives.

Specifically, the L-amino acid may be L-lysine or L-threonine.

Specifically, the ratio of L-lysine or L-threonine:riboflavin in the feed or feed additive may be 1:0.0001-0.01 as described above.

The feed of the present invention can be prepared by preparing a feed additive comprising the L-amino acid and riboflavin, and mixing the feed additive with feed or adding the feed additive directly to feed during the preparation of the feed. The L-amino and riboflavin in the feed of the present invention may be in a liquid or dry state, and specifically in the form of dry powder. Examples of a drying method that may be used in the present invention include, but are not limited to, air drying, natural drying, spray drying and freeze drying. The livestock feed may comprise, in addition to the L-amino acid and riboflavin of the present invention, conventional additives capable of enhancing the preservative property of the feed.

The feed additive of the present invention may further comprise non-pathogenic other microorganisms. Microorganisms that may be added to the feed additive of the present invention may be selected from the group consisting of *Bacillus subtilis* capable of producing protease, lipase and glucose-converting enzyme, *Lactobacillus* sp. that has physiological activity and organism-degrading ability in anaerobic conditions such as cow's stomach, filamentous fungi such as *Aspergillus oryzae* that shows the effects of increasing the weight of livestock, the production of milk and the digestion/absorption of the feed (J Animal Sci 43: 910-926, 1976), and yeast such as *Saccharomyces cerevisiae* (J Anim Sci 56:735-739, 1983).

Examples of feed containing the L-amino acid and riboflavin include, but are not limited to; vegetable feeds, such as grains, roots/fruits, food processing byproducts, algae, fibers, pharmaceutical byproducts, oils and fats, starches, gourds, and grain byproducts, and animal feeds such as proteins, inorganic materials, oils and fats, minerals, single-cell proteins, animal planktons, and food residue.

Feed additives comprising the L-amino acid and riboflavin of the present invention include, but are not limited to; a binder, an emulsifier and a preservative, which are added to prevent deterioration in quality, amino acids, vitamins, enzymes, probiotics, flavoring agents, non-protein nitrogenous compounds, silicates, buffer, colorants, extracting agents, and oligosaccharides, which are added to increase effects, and other feed mixture.

MODE FOR INVENTION

Hereinafter, the present invention will be described in further detail with reference to examples. It is to be understood, however, that these examples are for illustrative purposes only and are not intended to limit the scope of the present invention.

Example 1

Screening of Gluconic Acid Tolerant Strain by Artificial Mutagenesis

In this Example, in order to increase carbon flow in the pentose-phosphate pathway that is the major source of nicotinamide adenine dinucleotide phosphate (NADPH) required for the production of L-amino acid, an experiment for imparting adaptability for high-concentration of gluconic acid to the *Corynebacterium glutamicum* strain was performed.

An artificial mutation in KFCC10881 (Korean Patent No. 0159812), as a parent strain, was induced by N-methyl-N-nitro-N-nitroguanidine (NTG) and then the strain was cultured in the following plate medium containing 20 g/l of gluconic acid while strains that formed colonies faster than a control group not treated with NTG were isolated. In the case of the control group, the average diameter of colonies formed at 60 hours was about 0.5 mm, whereas in the case of the NTG-treated group, a diameter of colonies reached 1 mm within 40 hours of culture. Among the colonies, a colony having a deep yellow color unlike the control group was found, and thus it was expected that a mutant having a new character would be produced. This strain was named "*Corynebacterium glutamicum* CA01-2183", or "KFCC10881-YC", and was examined the cause of color development. The mutant strain, KFCC10881-YC, was deposited with the Korean Culture Center of Microorganisms (Yurim B/D, Honje 1-dong, Sudaemun-gu, Seoul, Korea) on Nov. 11, 2011 under the accession number KCCM11223P.

Composition of Plate Medium (pH 7.0)

20 g gluconic acid, 50 g $(NH_4)_2SO_4$, 10 g peptone, 5 g yeast extract, 1.5 g urea, 5 g $KH_2PO_4$, 10 g $K_2HPO_4$, 0.5 g $MgSO_4 \cdot 7H_2O$, 100 μg biotin, 1000 μg thiamine chloride, 2000 μg calcium-pantothenic acid, 2000 μg nicotinamide, and 20 g agar (per liter of distilled water).

Example 2

Analysis of the Lysine-producing Ability of KFCC10881-YC and Examination of Cause of Color Development In order to examine the characteristics of the KFCC10881-YC strain prepared in Example 1 above, the strain was cultured in the following manner to compare the Lysine-producing ability thereof, and the components of the culture medium were analyzed.

Specifically, each strain was inoculated into a 250-ml corner-baffle flask containing 25 ml of seed medium, and then cultured at 30° C. for 20 hours with shaking at 200 rpm. Next, 1 ml of the seed culture was inoculated into a 250-ml corner-baffle flask containing 24 ml of production medium and cultured at 30° C. for 72 hours with shaking at 200 rpm. The compositions of the seed medium and the production medium are as follows.

Composition of Seed Medium (pH 7.0)

20 g glucose, 10 g peptone, 5 g yeast extract, 1.5 g urea, 4 g $KH_2PO_4$, 8 g $K_2HPO_4$, 0.5 g $MgSO_4 \cdot 7H_2O$, 100 μg biotin, 1000 μg thiamine HCl, 2000 μg calcium-pantothenic acid, and 2000 μg nicotinamide (per liter of distilled water)

Composition of Production Medium (pH 7.0)

100 g glucose, 40 g $(NH_4)_2SO_4$, 2.5 g soybean extract, 5 g corn steep solids, 3 g urea, 1 g $KH_2PO_4$, 0.5 g $MgSO_4 \cdot 7H_2O$, 100 μg biotin, 1000 μg thiamine HCl, 2000 μg calcium-pantothenic acid, 3000 μg nicotinamide, and 30 g $CaCO_3$ (per liter of distilled water).

After completion of the culture, the KFCC10881-YC strain maintained the deep yellow color, and the culture supernatant also had a deep yellow color, unlike the culture medium of the control KFCC10881. Accordingly, the present inventors assumed that the material causing this color development would be contained in the culture medium. To verify this assumption, the concentrations of carotinoids and riboflavin that influence the color development in the microorganism were analyzed. As a result, the concentration of riboflavin in the culture medium showed a clear difference from that in the control, and there was no significant difference in the concentration of carotenoids. The concentrations of L-lysine and riboflavin analyzed by HPLC were shown in Table 1 below.

TABLE 1

| | | Concentrations of L-lysine and riboflavin produced in KFC10881-YC | | | | | | | |
|---|---|---|---|---|---|---|---|---|---|
| Test | | L-lysine (g/l) | | | | Riboflavin (mg/l) | | | |
| group | Strain | Batch 1 | Batch 2 | Batch 3 | Average | Batch 1 | Batch 2 | Batch 3 | Average |
| 1 | KFC10881 | 43.1 | 4.35 | 44.1 | 43.5 | 3.4 | 3.5 | 3.0 | 3.3 |
| 2 | KFCC10881-YC | 43.7 | 44.3 | 42.8 | 43.6 | 191.2 | 187.5 | 189.0 | 189.2 |

As a result, as seen from the Table 1, the average concentration of L-lysine in KFCC10881-YC was similar to that in the L-lysine-producing strain KFCC10881, but the average concentration of riboflavin in KFCC10881-YC increased by 57 times. Thus, it could be seen that the deep yellow color of the colony, which is the distinct characteristic distinguished from the parent strain, is attributable to the increased in concentration of riboflavin.

Example 3

Examination of Modification in Promoter Upstream of Rib Operon of Strain Producing High Concentration of Riboflavin, and Construction of a Vector for Chromosomal Integration of the Modified Promoter (Pmrb)

In order to investigate the nucleotide mutation that induced the color change and increased the riboflavin producing ability in the KFCC10881-YC strain prepared in Example 1, nucleotide sequence of the chromosomal region related to the riboflavin biosynthesis in the *Corynebacterium glutamicum* sp. KFCC10881-YC strain was determined and confirmed based on the NIH GenBank database.

As a result, it was found that $-10^{th}$ and $-16^{th}$ nucleotide residues from the initiation codon of the rpe gene located upstream of the rib operon had a G-to-A substitution and a G-to-T substitution, respectively. The promoter having the two nucleotide substitution in the expected region of the rib operon promoter was named "Pmrb" (SEQ ID NO: 5).

In order to examine the effect of increase in riboflavin concentration by increases in the expression inducing activity and enzymatic activity of the Pmrb promoter having the nucleotide substitutions, a vector for introducing the promoter into the chromosome was constructed.

Based on the reported nucleotide sequence, a primer having an EcoRI restriction enzyme site inserted into the 5' end and a primer having a SalI restriction enzyme site inserted into the 3' end (SEQ ID NOS: 7 and 8) were synthesized. Using the promoters, PCR was performed with the chromosome of IFCC10881-YC as a template to amplify an about 650-bp Pm-rpe gene fragment including a 350-bp region expected to be the rib operon promoter. The PCR was performed under the following conditions: initial denaturation at 94° C. for 5 minutes, and then 30 cycles, each consisting of denaturation at 94° C. for 30 sec, annealing at 56° C. for 30 sec, and extension at 72° C. for 40 sec, followed by final extension at 72° C. for 7 min. The primers used in the PCR are as follows.

SEQ ID NO. 7: 5'-tttgaattcgtgtgcgtgcaggtttctc-3'
SEQ ID NO. 8: 5'-tttgtcgacattccgctaaaacacgt-3'

Figure 3:
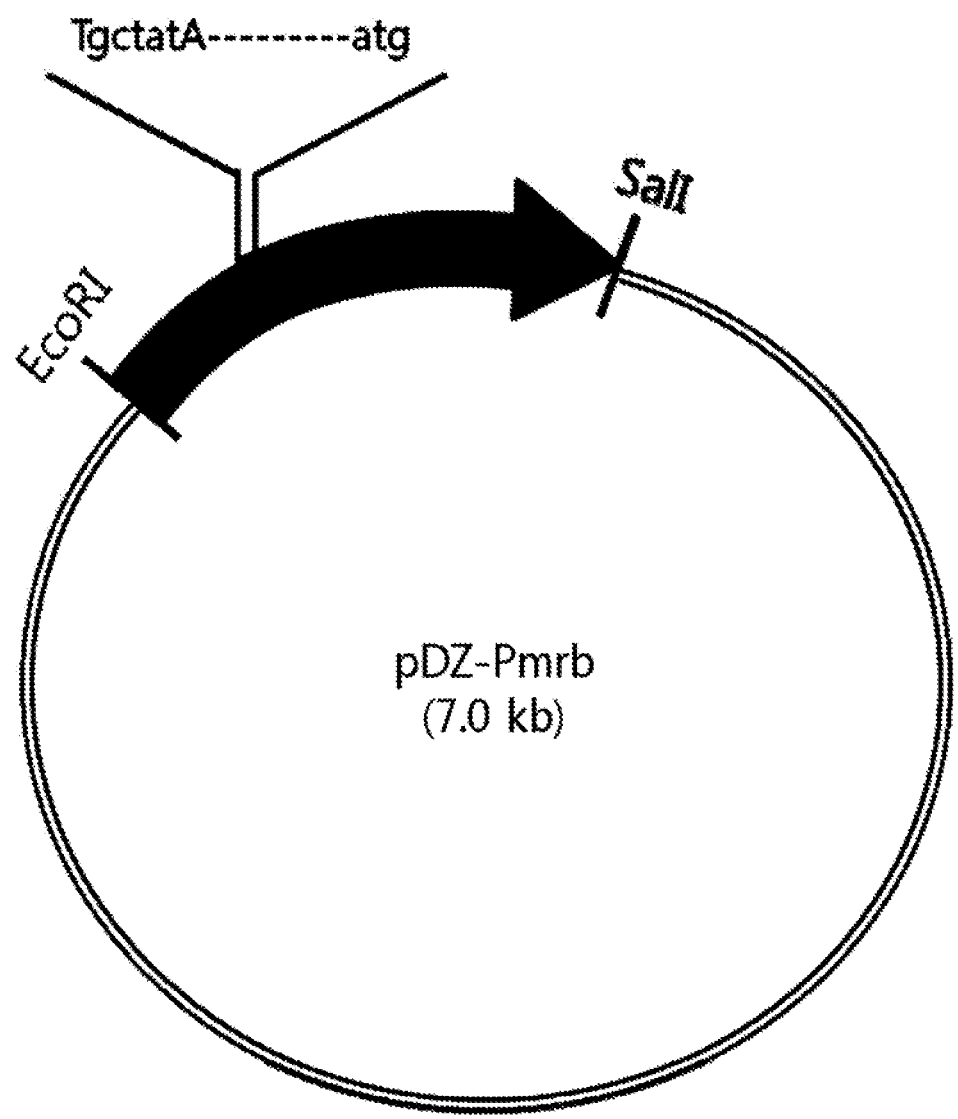
FIG. 3 shows a pDZ-Pmrb vector constructed in order to insert a promoter of SEQ ID NO: 5.

The gene fragment amplified by PCR was treated with the restriction enzymes EcoRI and SalI to obtain a DNA fragment, which was then ligated with a pDZ vector (Forean Patent Publication No. 2009-0094433), which has the EcoRI and SalI sites at the ends, for introduction into the chromosome. Then, the vector was transformed into *E. coli* DH5α, which was then plated on LB solid medium containing kanamycin (25 mg/l). A colony transformed with the vector comprising the desired gene was screened by PCR, and then a plasmid was obtained using a conventional plasmid extraction method known in the art. This plasmid was named "pDZ-Pmrb" (FIG. 3).

Example 4

Construction of a Strain Having Pmrb Introduced into Upstream of Rib Operon in Chromosome of High-concentration Lysine-producing Strain and Comparison of Lysine and Riboflavin Productivities The vector pDZ-Pmrb prepared in Example 3 was transformed into the L-lysine-producing strain *Corynebacterium glutamicum* KFCC10881 by homologous chromosomal recombination. Then, a strain having a rib operon promoter mutation introduced into the chromosome was separated based on a change in the color of colonies and cultured in the same manner as described in Example 2, and the concentrations of L-lysine and riboflavin recovered from the culture were analyzed (Table 2). The strain, the rib operon promoter mutation introduced therein, was named "*Corynebacterium glutamicum* CA01-2162" or "KFCC10881::Pmrb". The mutant strain, KFCC10881::Pmrb, was deposited with the Korean Culture Center of Microorganisms (Yurim B/D, Honje 1-dong, Sudaemun-gu, Seoul, Korea) on Nov. 11, 2011 under the accession number KCCM11221P.

TABLE 2

Anaylsis of production of L-lysine and riboflavin by introduction of promoter mutation

| Test group | Strain | L-lysine (g/l) | | | | Riboflavin (mg/l) | | | |
|---|---|---|---|---|---|---|---|---|---|
| | | Batch 1 | Batch 2 | Batch 3 | Average | Batch 1 | Batch 2 | Batch 3 | Average |
| 3 | KFC10881 | 42.1 | 42.6 | 43.1 | 42.6 | 3.1 | 3.3 | 3.0 | 3.1 |
| 4 | KFC10881::Pmrb | 42.7 | 42.3 | 42.8 | 42.6 | 200.2 | 186.3 | 189.0 | 192.1 |

As a result, as seen from the Table 2 above, the average concentration of L-lysine in the case of KFCC10881::Pmrb (test group 4) introduced with the promoter Pmrb having the two nucleotide substitution mutations did not change compared to that in the control KFCC10881 (test group 3) having the wild-type rpe gene promoter, but the average concentration of riboflavin in test group 4 increased by about 61 times.

Example 5

Construction of a Vector to Introduce Strong Promoter (LysCP1) into Upstream of ribG in Rib Operon In order to overexpress only the riboflavin biosynthesis group gene excluding the rpe gene, a strong promoter derived from *Corynebacterium* was ligated to the initiation codon of the ribG gene (SEQ ID NO: 4) located in the front of the rib biosynthesis gene family, thereby constructing a recombinant vector for inducing the expression of the riboflavin biosynthesis gene family.

To obtain a ribG gene fragment derived from *Corynebacterium glutamicum*, the chromosomal DNA of *Corynebacterium glutamicum* KFCC10881 was prepared as a template, and primers (SEQ ID NOS: 9 and 10) designed to have an EcoRI restriction enzyme site at the 5' end and a XbaI restriction enzyme site at the 3' end were synthesized. PCR was performed using the synthesized primers to obtain a DNA fragment comprising a 300-bp region upstream of the initiation codon of the ribG gene. Also, primers (SEQ ID NOS: 11 and 12) designed to have XbaI and NdeI restriction enzyme sites at the 5' end and a SalI restriction enzyme site at the 3' end were synthesized, and PCR was performed using the synthesized primers to obtain a 300-bp fragment comprising the initiation codon of the ribG gene. The PCR was performed under the following conditions: initial denaturation at 94° C. for 5 min, and then 30 cycles, each consisting of denaturation at 94° C. for 30 sec, annealing at 56° C. for 30 sec, and extension at 72° C. for 30 sec, followed by final extension at 72° C. for 7 min. The two PCR products were treated with EcoRI and XbaI, and XbaI and SalI, respectively, and then ligated with a DNA fragment obtained by treating a pDZ vector with the restriction enzymes SalI and EcoRI, thereby constructing a pDZ-ribG vector. The primer sequences used in this PCR are as follows:

SEQ ID NO. 9:
5'- tttgaattcgtgtgcgtgcaggtttctcc-3'

SEQ ID NO. 10:
5'- tttctagattactgcgcgagtgctc-3'

-continued

SEQ ID NO. 11:
5'- ttttctagataacatatggatgttgcgcacgcg-3'

SEQ ID NO. 12:
5'- tttgtcgacattggcgtaaaacacgt-3'

Figure 4:
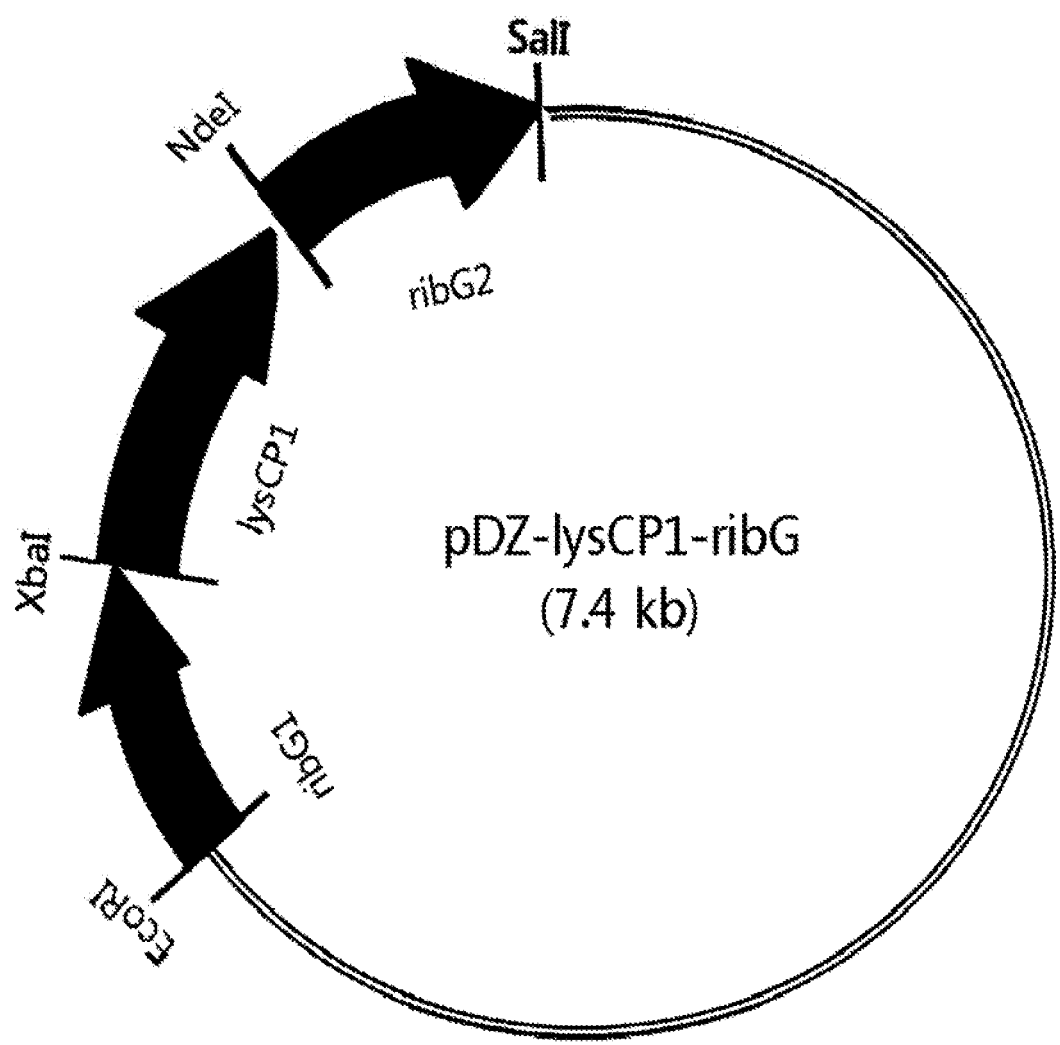
FIG. 4 shows a pDZ-lysCP1-ribG vector constructed in order to insert a promoter of SEQ ID NO: 6.

Primers (SEQ ID NOS: 13 and 14) designed to amplify the *Corynebacterium glutamicum*-derived lysCP1 promoter (SEQ ID NO: 6) and to have an XbaI restriction enzyme site inserted into the 5' end and a NdeI restriction enzyme site inserted into the 3' end were synthesized. Using the primers, PCR was performed with the chromosomal DNA of the *Corynebacterium glutamicum* strain as a template to amplify an about 400-bp promoter fragment. The PCR was performed under the following conditions: initial denaturation at 94° C. for 5 min, and then 30 cycles, each consisting of denaturation at 94° C. for 0.30 sec, annealing at 58° C. for 30, and extension at 72° C. for 30 sec, followed by final extension at 72° C. for 7 min. The PCR amplification product was treated with XbaI and NdeI, and then ligated with a DNA fragment obtained by treating a pDZ-ribG vector with XbaI and NdeI, thereby constructing a pDZ-lysCP1_ribG vector (FIG. 4). The primer sequences used in the PCR are as follows:

SEQ ID NO. 13:
5'-ttttctagatagggagccatcttttgggg-3'

SEQ ID NO. 14:
5'-tttcatatgctttgtgcacctttcg-3'

Example 6

Comparison of Lysine and Riboflavin Productivities of a Strain Having Strong Promoter (LysCP1) Introduced into Upstream of ribG The vector pDZ-lysCP1_ribG prepared in Example 5 was transformed into the L-lysine-producing strain *Corynebacterium glutamicum* KFCC10881 by an electric pulse method. A strain having lysCP1 substituting for the inherent promoter of the chromosomal ribG gene was selectively isolated, thereby obtaining KFCC10881::lysCP1_ribG that produces both L-lysine and riboflavin. This strain was cultured in the same manner as described in Example 2, and the concentrations of L-lysine and riboflavin in the culture medium were analyzed (Table 3). The KFCC10881::lysCP1_ribG strain was named "*Corynebacterium glutamicum* CA01-2161" or "KFCC10881::lysCP1_ribG". This mutant strain, KECC10881::lysCP1_ribG, was deposited with the Korean Culture Center of Microorganisms (Yurim B/D, Honje 1-dong, Sudaemun-gu, Seoul, Korea) on Nov. 11, 2011 under the accession number KCCM11220P.

TABLE 3

| Analysis of production of L-lysine and riboflavin by introduction of promoter | | | | | | | | |
|---|---|---|---|---|---|---|---|---|
| Test | | L-lysine (g/l) | | | | Riboflavin (mg/l) | | |
| group | Strain | Batch 1 | Batch 2 | Batch 3 | Average | Batch 1 | Batch 2 | Batch 3 | Average |
| 5 | KFC10881 | 43.7 | 42.5 | 43.1 | 43.1 | 3.4 | 3.5 | 3.0 | 3.3 |
| 6 | KFC10881::lysCP1_ribG | 43.7 | 43.4 | 42.7 | 43.3 | 237.2 | 247.5 | 241.0 | 241.9 |

As a result, as shown in Table 3 above, when RibG was overexpressed using the lysCP1 promoter (test group 6), the average concentration of L-lysine rarely changed compared to that in the control KFCC10881 (test group 5) having the wild-type promoter, but the concentration of riboflavin increased by about 73 times.

Thus, it could be seen that, when the riboflavin biosynthesis operon was overexpressed using the heterogeneous promoter, the production of riboflavin could be greatly increased without influencing the production of lysine, and as the expression inducing activity of the promoter became stronger, the production of riboflavin increased by overexpression of the riboflavin biosynthesis gene family.

Example 7

Comparison of Lysine and Riboflavin Productivities of a Strain Having Increased Copy Number of Rib Operon A plasmid comprising the rib operon was introduced into the KFCC10881 strain to increase the copy number of the riboflavin biosynthesis gene, and the riboflavin production ability of the strain was examined.

Based on the reported nucleotide sequence, a primer having a XbaI restriction enzyme site inserted into the 5' end and a primer having the same restriction enzyme site inserted into the 3' end (SEQ ID NOS: 15 and 16) were synthesized, and using the primers, PCR was performed with the chromosome of KFCC10881 as a template to amplify an about 4500-bp rib operon. The PCR was performed under the following conditions: initial. denaturation at 94° C. for 5 min, and then 30 cycles, each consisting of denaturation at 94° C. for 30 sec, annealing at 56° C. for 30 sec, and extension at 72° C. for 4 min, followed by final extension at 72° C. for 7 min. The primer sequences used in the PCR are as follows:

```
SEQ ID NO. 15:
5'-TTTGGTACCGATTGAAAAGTCCGTGCGTG-3';

SEQ ID NO. 16:
5'-TTTGGTACCCGCGATCTTTTTCAGAAACT-3'
```

The gene fragment amplified by PCR was treated with the restriction enzyme XbaI to obtain a DNA fragment. The DNA fragment was ligated with a pECCG117 vector having the XbaI restriction sites at the ends, and the vector was transformed into *E. coli* DH5α, then plated on LB solid medium containing kanamycin (25 mg/l). Then, a colony transformed with the vector comprising the desired gene were screened by PCR, and then a plasmid was obtained using a conventional plasmid extraction method known in the art. This plasmid was named "pECCG117-rib".

The vector pECCG117-rib prepared as described above was introduced into the KFCC10881 strain by an electric pulse method and cultured in the same manner as described in Example 2, and the concentrations of L-lysine and riboflavin in the culture medium were analyzed (Table 4).

TABLE 4

Analysis of production of L-lysine and riboflavin by introduction of plasmid

| Test group | Strain | L-lysine (g/l) | | | | Riboflavin (mg/l) | | | |
|---|---|---|---|---|---|---|---|---|---|
| | | Batch 1 | Batch 2 | Batch 3 | Average | Batch 1 | Batch 2 | Batch 3 | Average |
| 7 | KFC10881/ pECCG117 | 43.1 | 43.1 | 42.5 | 32.9 | 4.0 | 3.2 | 3.6 | 3.6 |
| 8 | KFCC10881/ pECCG117-rib | 42.7 | 42.4 | 43.7 | 42.9 | 245.1 | 231.2 | 238.3 | 238.5 |

As a result, as seen in Table 4 above, in the case in which the copy number of the rib operon was increased by introduction of the plasmid (test group 8), the average concentration of L-lysine rarely changed compared to the control KFCC10881::pECCG117 (test group 7) containing no rib operon, but the concentration of riboflavin increased by about 66 times.

Thus, it could be seen that, when the riboflavin biosynthesis gene was overexpressed by increasing the copy number of the riboflavin biosynthesis operon using the plasmid, the production of riboflavin in the strain can be greatly increased without influencing the production of the lysine.

Example 8

Construction of AH-resistant L-threonine-producing Strain by Artificial Mutagenesis In this Example, in order to increase the L-threonine-producing ability of *Corynebacterium glutamicum*, an experiment for imparting resistance to the L-threonine analogue AHV (2-amino-3-hydroxy-valerate) was performed. Specifically, an artificial mutation in KFCC10881 as a parent strain was induced by N-methyl-N-nitro-N-nitroguanidine (NTG), and then the strain was cultured in minimal medium containing 1-10 g/l of AHV, while whether colonies were formed at various concentrations of AHV was analyzed in comparison with a control group not treated with NTG. The control group not treated with NTG showed resistance to 1-3 g/l of AHV at 72 hours of culture, but in the NTG-treated group, colonies were formed up to an AHV concentration of 6 g/l at the same time point. In order to examine whether the L-threonine-producing ability of the strains increased or not, the strains were cultured in the following manner, and the production of L-threonine was analyzed.

Each of the strains was inoculated into a 250-ml corner-baffle flask containing 25 ml of seed medium and cultured at 30° C. for 20 hours with shaking at 200 rpm. Thereafter, 1 ml of the seed culture was inoculated into a 250-ml corner-baffle flask containing 24 ml of production medium and culture at 30° C. for 48 hours with shaking at 200 rpm. The compositions of the seed medium and the production medium are as follows.

Composition of Minimal Medium (pH 7.2)

5 g glucose, 1 g KH$_2$PO$_4$, 5 g (NH$_4$)$_2$SO$_4$, 0.4 g MgSO$_4$ 7H$_2$O, 0.5 g NaCl, 200 µg biotin, 100 µg thiamine HCl, 100 µg calcium-pantothenic acid, 0.03 g nicotinamide, 0.01 g L-threonine, 2 g urea, 0.09 mg Na$_2$B$_4$O$_7$10H$_2$O, 0.04 mg (NH$_4$)$_6$Mo$_7$O$_{27}$4H$_2$O, 0.01 mg ZnSO$_4$7H$_2$O, 0.01 mg CuSO$_4$5H$_2$O, 0.01 mg MnCl$_2$4H$_2$O, 1 mg FeCl$_3$6H$_2$O, and 0.01 mg CaCl$_2$ (per liter of distilled water).

Composition of Seed Medium (pH 7.0)

20 g glucose, 10 g peptone, 5 g yeast extract, 1.5 g urea, 4 g KH$_2$PO$_4$, 8 g K$_2$HPO$_4$, 0.5 g MgSO$_4$ 7H$_2$O, 100 µg biotin, 1000 µg thiamine HCl, 2000 µg calcium-pantothenic acid, and 2000 µg nicotinamide (per liter of distilled water).

Composition of Production Medium (pH 7.0)

1.00 g glucose, 20 g (NH$_4$)$_2$SO$_4$, 2.5 g soybean protein, 5 g corn steep solids, 3 g urea, 1 g KH$_2$PO$_4$, 0.5 g MgSO$_4$7H$_2$O, 100 µg biotin, 1000 µg thiamine HCl, 2000 µg calcium-pantothenic acid, 3000 µg nicotinamide, and 30 g CaCO$_3$ (per liter of distilled water).

After completion of culture, the concentration of L-threonine in the culture medium was analyzed by HPLC, and the mutant strain, showing the highest L-threonine production ability, was named "*Corynebacterium glutamicum* CA01-2182" or "KFCC10881-THR". The mutant strain, KFCC10881-THR, was deposited with the Korean Culture Center of Microorganisms (Yurim B/D, Honje 1-dong, Sudaemun-gu, Seoul, Korea) on Nov. 11, 2011 under the accession number KCCM11222P. The L-threonine-producing ability of KFCC10881-THR is shown in Table 5 below.

TABLE 5

Concentration of L-threonine produced in KFCC10881-THR

| Test group | Strain | L-threonine (g/l) | | |
|---|---|---|---|---|
| | | Batch 1 | Batch 2 | Batch 3 |
| 9 | KFCC10881 | 1.2 | 1.5 | 1.4 |
| 10 | KFCC10881-THR | 6.7 | 7.1 | 7.0 |

In Table 5 above, test group 9 indicates the average concentration of L-threonine in the control KFCC10881, and test group 10 indicates the average concentration of L-threonine in KFCC1088-THR.

As a result, as seen from the Table 5 above, the production of L-threonine in KFCC10881-THR increased by about 5.6 g/l compared to that in KFCC10881.

Example 9

Construction of Strains Introducing Strong Promoter into Upstream of Rib Operon or Upstream of ribG in Chromosome, and Comparison of Threonine and Riboflavin Productivities Each of the vector pDZ-Pmrb prepared in Example 3 and the vector pDZ-lysCP1_ribG prepared in Example 5 was transformed into the L-threonine-producing strain KFCC10881-THR (prepared in Example 8) by an electric pulse method. Then, a strain having Pmrb substituting for the wild-type promoter of the chromosomal rpe gene, or a strain having lysCP1 substituting for the wild-type promoter of the ribG gene, was selectively isolated and was cultured in the same manner as described in Example 7. The concentrations of L-threonine and riboflavin in the culture medium were analyzed (Table 6).

TABLE 6

Analysis of production of L-threonine and ribloflavin by introduction of mutation into promoter

| Test group | Strain | L-threonine (g/l) | | | Riboflavin (mg/l) | | |
|---|---|---|---|---|---|---|---|
| | | Batch 1 | Batch 2 | Batch 3 | Batch 1 | Batch 2 | Batch 3 |
| 11 | KFC10881-THR | 6.9 | 6.8 | 7.0 | 3.2 | 3.1 | 3.3 |
| 12 | KFC10881-THR::Pmrb | 7.1 | 6.8 | 7.1 | 180.0 | 177.5 | 179.2 |
| 13 | KFC10881-THR::lysCP1_ribG | 6.7 | 7.2 | 6.9 | 214.2 | 203.5 | 213.0 |

As a result, as seen from the Table 6 above, in the case of KFCC10881::Pmrb (test group 12) comprising the promoter Pmrb having two nucleotide substitution mutations, and KPCC10881-THR::lysCP1_ribG (test group 13) having RibG overexpressed by the lysCP1 promoter, the average concentrations of L-threonine in the mutant strains rarely changed compared to that in the control KFCC10881-THR (test group 11) having the wild-type promoters of the rpe and ribG genes, but the average concentrations of riboflavin in the mutant strains increased by about 56 times and 66 times, respectively.

The above-described results indicate that, when the riboflavin biosynthesis operon is overexpressed, the production of riboflavin can be greatly increased without influencing the production of L-threonine, thereby producing L-threonine and riboflavin at the same time. Thus, it can be seen that, as the expression-inducing activity of the riboflavin biosynthesis operon promoter in the L-threonine-producing strain becomes stronger, the production of riboflavin is increased by the overexpression of the riboflavin biosynthesis gene family.

The invention claimed is:

1. A modified *Corynebacterium glutamicum* microorganism for simultaneously producing L-lysine or L-threonine, and riboflavin, wherein said modified *Corynebacterium glutamicum* microorganism has enhanced expression of a riboflavin (rib) operon as compared to the expression of a rib operon in a corresponding wild-type *Corynebacterium glutamicum* microorganism, wherein the rib operon comprises genes encoding riboflavin biosynthesis enzymes, and wherein the expression of the rib operon in said modified *Corynebacterium glutamicum* microorganism is enhanced by increasing intracellular copy number of the genes of the rib operon, replacing the native promoter of the rib operon with a stronger promoter, and a combination thereof, wherein said modified *Corynebacterium glutamicum* microorganism has increased L-lysine or L-threonine-producing ability as compared to a corresponding wild-type *Corynebacterium glutamicum* microorganism, and wherein the concentration of riboflavin produced by said modified *Corynebacterium glutamicum* microorganism is increased by 56 to 73-fold as compared to the concentration of riboflavin produced by a corresponding wild-type *Corynebacterium glutamicum* microorganism under the same conditions, while maintaining the increased production of L-lysine or L-threonine as compared to a corresponding wild-type *Corynebacterium glutamicum* microorganism.

2. The microorganism according to claim 1, wherein the expression of the rib operon in said modified *Corynebacterium glutamicum* microorganism is enhanced by replacing the native promoter of the rib operon with a stronger promoter.

3. The microorganism according to claim 2, wherein the stronger promoter comprises the nucleotide sequence of SEQ ID NO: 5 or 6.

4. The microorganism according to claim 1, wherein the modified *Corynebacterium glutamicum* microorganism is the microorganism deposited with Korean Culture Center of Microorganisms (KCCM) under accession No. KCCM11220P, KCCM11221P or KCCM11223P.

5. A method for producing L-lysine or L-threonine, and riboflavin, comprising:
   a) culturing the modified *Corynebacterium glutamicum* microorganism of claim 1 in a culture medium; and
   b) producing L-lysine or L-threonine, and riboflavin by a fermentation process.

6. The method according to claim 5, which further comprises granulating the fermented culture medium comprising L-lysine or L-threonine, and riboflavin.

7. The method according to claim 5, which further comprises removing a bacterial sludge from the fermented culture medium comprising L-lysine or L-threonine, and riboflavin.

* * * * *